United States Patent
Patil et al.

(10) Patent No.: US 11,892,326 B1
(45) Date of Patent: Feb. 6, 2024

(54) TOCODYNAMOMETER TRANSDUCER

(71) Applicant: Aronix LLC, Peachtree Corners, GA (US)

(72) Inventors: Arun Narayan Patil, Winder, GA (US); Anand Raghunath Bhave, Pune (IN); Sunanda Narayan Patil, Pune (IN); Pratibha Narayan Patil, Pune (IN)

(73) Assignee: Aronix LLC, Peachtree Corners, GA (US)

( * ) Notice: Subject to any disclaimer, the term of this patent is extended or adjusted under 35 U.S.C. 154(b) by 0 days.

(21) Appl. No.: 17/962,812

(22) Filed: Oct. 10, 2022

(51) Int. Cl.
*G01D 5/22* (2006.01)
*A61B 5/00* (2006.01)
*A61B 5/11* (2006.01)

(52) U.S. Cl.
CPC .......... *G01D 5/2291* (2013.01); *A61B 5/1107* (2013.01); *A61B 5/4356* (2013.01); *A61B 5/6831* (2013.01); *A61B 2562/0247* (2013.01); *A61B 2562/125* (2013.01)

(58) Field of Classification Search
CPC ... G01D 5/2291; A61B 5/1107; A61B 5/4356; A61B 5/6831; A61B 2562/0247; A61B 2562/125; A61B 2562/16–168; A61B 5/43–4362; A61B 5/02411; A61B 2562/02

See application file for complete search history.

(56) References Cited

U.S. PATENT DOCUMENTS

| | | | |
|---|---|---|---|
| 4,354,506 A | 10/1982 | Sakaguchi et al. | |
| 4,640,295 A | 2/1987 | Isaacson | |
| 4,966,152 A | 10/1990 | Gang et al. | |
| 5,070,888 A * | 12/1991 | Hon | A61B 8/4236 600/588 |
| 5,205,296 A * | 4/1993 | Dukes | A61B 5/4356 600/588 |
| 6,048,323 A * | 4/2000 | Hon | A61B 8/4227 600/588 |
| 9,717,412 B2 | 8/2017 | Roham et al. | |

* cited by examiner

*Primary Examiner* — Eric F Winakur
*Assistant Examiner* — Abid A Mustansir
(74) *Attorney, Agent, or Firm* — H. Brock Kolls

(57) ABSTRACT

The present invention relates to an improved tocodynamometer transducer that exhibits increased mechanical stability, dynamic range, accuracy, and reliability. Improvement components include top and bottom enclosures, plunger, ferrite core, LVDT transformer, transformer housing, flat spring, and other components. The flat spring includes four spring ribs that are symmetrical, curvilinear in shape, identical in path length, separated by an air gap, and equally spaced between the outer ring, inner ring, and the spring ribs that are adjacent. The spring constant is identical along two or more axes improving the accuracy of the improved tocodynamometer transducer. The ferrite core travel length is increased and mechanically constrained to remain between the LVDT transforming winding increasing the dynamic range and the linearity of the voltage output of the improved tocodynamometer transducer.

20 Claims, 18 Drawing Sheets

322  324

TOCODYNAMOMETER TRANSDUCER

TECHNICAL FIELD OF THE INVENTION

This invention relates to an improved tocodynamometer transducer, and particularly to component improvements that together increase the mechanical stability, dynamic range, accuracy, and reliability of the transducer.

BACKGROUND OF THE INVENTION

In gynecology and obstetrics, two medical parameters are important to assess the condition of the fetus. These two parameters are the fetal heart rate measured via an ultrasound Doppler signal and uterus (or labor) activity. Simultaneous assessment of the fetal heart rate (FHR) and uterus activity (Tocodynamometer) allows an informed determination of the fetal condition. Monitors measuring and recording both parameters are called Cardiotocographs (CTG monitors) or in general, Fetal Monitors.

For pre-birth applications, the most common method to obtain fetal heart rate is by using an ultrasound (US) transducer which is to be placed externally on the pregnant woman's abdomen. The ultrasound signal is received by piezo-electric crystals and appropriately filtered. As the heart rate signal is contained in the-very noisy-received ultrasound Doppler signal, the ultrasound transducer must be placed directly over the fetal heart, for example, on the lower left part of the abdomen.

Uterus activity is obtained by way of a tocodynamometer transducer which is to be placed externally on the fundus uteri. For example, approximately centrally on the abdomen. A Tocodynamometer transducer is a tension measuring device, that uses one or more resistive wire strain gauges (in half or full bridge configuration) or a Linear Variable Differential Transformer (LVDT) in the transducer design. The values measured by these transducers are not absolute pressure measurements as uterus 'hardness' as well as uterus deformation (and sometimes also respiration) influence the tension, but still, it is possible to obtain clinically relevant results, for example, the frequency, magnitude (weak, moderate, strong) and pattern of such contractions can be valuable to the physician, as a measure of the normal progression of labor. Additionally, it provides a guide for nurses and physicians in the use of medication or the need for other remedial actions.

Before our invention, a tocodynamometer transducer was used for monitoring the extra-uterine activity of a woman during pregnancy and labor. These prior tocodynamometer transducers however had several inherent shortcomings. One shortcoming of the older tocodynamometer transducer is the flat spring design. Prior flat springs only had one axis of equal spring constant. As such, the same force applied to the edges of the diaphragm produces an unequal deflection of the diaphragm depending on where on the diaphragm the force was applied resulting in inaccurate readings. In addition, the prior flat springs had a very short range of linear spring constant and varied from unit to unit.

Another shortcoming of the prior flat spring is that a prior plastic adapter has prongs that fit through holes in the prior spring. Once fitted, the prior plastic adapter is affixed to the prior flat spring by way of heat welding the plastic which melts the prongs to prevent the removal of the adapter from the spring. Such heat welding introduces stresses in the prior flat spring metal which creates variations in spring constant from unit to unit and over a period of time loses elastic property with physical deformation that causes a permanent offset in the LVDT output (as spring does not come back to home position).

Another shortcoming is that the length of the prior ferrite core used in combination with the prior LVDT transformer breaches the boundary created by the prior LVDT transformer wire windings. When this occurs the prior ferrite material out of the boundary of the prior wire windings couples the magnetic flux to the magnetic shielding case causing the readings from the prior tocodynamometer transducer to become non-linear and inaccurate.

Another shortcoming is that the length of the prior ferrite core used in combination with the prior LVDT transformer is more than double the size in length required causing the LVDT output to drift. In this regard, whether the diaphragm has a force applied to it or not the LVDT output has a slow drift as the ferrite core portion sticks out of the LVDT bore picking up electromagnetic interference (EMI).

Another shortcoming is that the prior plunger comprises a raised step collar that limits the range of motion of the prior ferrite core within the prior LVDT transformer. Hence, the dynamic range of the prior tocodynamometer transducer is limited by restricting the movable range of the prior ferrite core. As a result, in addition to being less accurate, it was also more difficult to position and secure the prior tocodynamometer transducer to a pregnant woman without inadvertently applying too much pressure on the diaphragm which limits the diaphragm range of travel negatively impacts the ability to receive accurate readings from the prior tocodynamometer transducer.

Another shortcoming is that the supply voltage to the tocodynamometer transducer is fixed at +4.0 volts (V) direct current (DC) but the prior tocodynamometer transducer electrical circuit comprises at least one semiconductor component rated for a minimum supply voltage of +5.0V DC. As such, these under-voltage operational conditions cause variation and fluctuation in semiconductor performance that can impact the accuracy and reliability of the prior tocodynamometer transducer.

Another shortcoming is resultant of these shortcomings with the prior flat spring, prior ferrite core, prior plunger, and prior electrical circuit design. Therefore, the tocodynamometer transducer output is not linear across the range of motion of the diaphragm and is unnecessarily limited to forces or operation to between 0 grams (gm) and 150 gm.

Another shortcoming is in the mechanical stability of the prior tocodynamometer transducer. The use of self-tapping screws into plastic cause undesirable angular forces, and misalignment of critical surfaces that need to be co-planar for accurate operation. In addition, such self-tapping screws tend to loosen within the plastic over time causing accuracy and output drift.

Another shortcoming in mechanical stability is moisture ingress through improperly sealed enclosure edges that cause premature corrosion of key components, degradation, and spurious/intermittent output response of the prior tocodynamometer transducer.

Another shortcoming with the prior tocodynamometer transducer was the prior standoffs used for mounting components could touch other components unintentionally which impacted the prior tocodynamometer transducer accuracy and contributed to calibration drift over time. In this regard, one example is the prior printed circuit board that comprises the prior electrical circuit that can touch and bind against the prior standoff. Such binding can cause misalignment and stresses that can introduce errors into readings from the prior tocodynamometer transducer by flexing and/or loosening the prior printed circuit board, moving the sensitive prior LVDT transform when pressure is placed or changed on the prior tocodynamometer transducer enclosure like when positioning and securing the prior tocodynamometer transducer onto a patient.

The present invention addresses these and other shortcomings by providing an improved tocodynamometer transducer. For these reasons and shortcomings as well as other reasons and shortcomings there is a long-felt need that gives rise to the present invention.

SUMMARY OF THE INVENTION

The shortcomings of the prior art are overcome and additional advantages are provided through the provision of an improved tocodynamometer transducer comprising a bottom enclosure having a bottom internal side, a skin-contacting side, and a diaphragm opening therethrough. A top enclosure has a top exterior surface and a top internal surface.

A diaphragm is circular in shape, the diaphragm comprises a flexible relief channel integrally formed in the diaphragm proximate to the perimeter of the diaphragm defining a diaphragm deflection area, the diaphragm is secured within the diaphragm opening.

A plunger comprises a shaft having a shaft hole along the length of the shaft that is threaded, and a deflection surface having a plunger top side and a plunger bottom side. A ferrite core is threaded around the outer circumference and solid in composition, the ferrite core is screwed into the shaft hole.

A transformer housing comprises a housing bottom that has a housing hole centrally located therethrough, an outer circumference surface, and a housing interior region.

A linear variable differential transformer has a circular air core. A magnetic shield enclosure comprises a top shield has a top shield hole, and a bottom shield has a shield interior region. The linear variable differential transformer is fitted into the shield interior region. The shaft of the plunger is placed through the housing hole, the bottom shield hole, the circular air core, and the top shield hole. The magnetic shield enclosure is fastened in the housing interior region. The plunger bottom side is placed in contact with the diaphragm deflection area.

A flat spring is formed from a single contiguous piece of metal. The flat spring comprises an outer ring, an inner ring, and four spring ribs. The outer ring has more than one spring mount hole. Each of the spring ribs is symmetrical, curvilinear in shape, identical in path length, separated by an air gap, and equally spaced between the outer ring, the inner ring, and the spring rib that are adjacent. Each of the spring ribs is connected, in an integrally formed manner, at a first end to the outer ring and a second end to the inner ring. The spring constant of the flat spring is predetermined by the thickness of the flat spring and identical along two or more axes with respect to the inner ring.

A spring washer comprises a threaded raised inner collar that is sized, fitted through the inner ring, and adhered to the flat spring. The shaft screws into and protrudes from the spring washer. The flat spring is fastened to the transformer housing. The top enclosure and the bottom enclosure are joined and secured together.

Additional shortcomings of the prior art are overcome and additional advantages are provided through the provision of an improved tocodynamometer transducer comprising more than one metal fastener, more than one threaded metal insert, and a bottom enclosure having a bottom internal side, a skin-contacting side, and a diaphragm opening therethrough.

A top enclosure has a top exterior side and a top internal side. More than one standoff is integrally formed on the top internal surface and the bottom internal surface. Each of the standoffs on the top internal surface is conical in shape and wider at the attachment point on the top internal surface. The threaded metal insert is fitted into each of the standoffs on the bottom internal surface.

A diaphragm is circular in shape, the diaphragm comprises a flexible relief channel integrally formed in the diaphragm proximate to the perimeter of the diaphragm defining a diaphragm deflection area. The diaphragm is secured within the diaphragm opening.

A plunger comprises a shaft having a shaft hole along the length of the shaft that is threaded, and a deflection surface having a plunger top side and a plunger bottom side, the plunger top side and the plunger bottom side are flat and absent raised embossed features. The deflection surface is circular in shape and sized to substantially fit within the deflection area. The shaft is circular in shape and uniform in diameter along the length of the shaft. The shaft is integrally attached to the center of the plunger top side forming a 90-degree angle between the shaft and the deflection surface around the circumference of the shaft. The shaft further comprises a thread pattern embossed around the outer circumference.

A ferrite core is threaded around the outer circumference and solid in composition, the ferrite core is screwed into the shaft hole. A transformer housing is circular in shape. The transformer housing comprises a housing bottom having a housing hole centrally located therethrough, an outer circumference surface, and a housing interior region. The housing bottom has a diaphragm facing the outer surface that is flat and absent raised embossed features maximizing the deflection distance between the plunger top side and the diaphragm facing the outer surface. More than one mounting tab has a transformer housing mounting hole therethrough. The mounting tabs are integrally formed along the outer circumference surface. More than one magnetic shield standoff and more than one spring standoff are integrally formed in the housing interior region. The threaded metal insert is fitted into each of the magnetic shield standoffs and the spring standoffs.

A linear variable differential transformer has a circular air core, a top wire winding edge, and a bottom wire winding edge that are defined by the location and length of a wire winding around the circular air core. The plunger transitions between a maximum deflection and a minimum deflection. During the maximum deflection, the ferrite core is positioned below the top wire winding edge and during a minimum deflection, the ferrite core is positioned above the bottom wire winding edge, wherein the ferrite core remains within the length of the wire winding of the linear variable differential transformer generating a linear voltage output across the plunger range of travel.

A magnetic shield enclosure comprises a top shield having a top shield hole that is centrally located and at least one shield mounting hole, and a bottom shield has a shield interior region and a bottom shield hole that is centrally located. The bottom shield hole is aligned with the top shield hole. The linear variable differential transformer is fitted into the shield interior region and the non-magnetic machine screw type of the metal fastener passes through the shield mounting hole and into the threaded metal insert that is fitted into the transformer mounting standoff securing the linear variable differential transformer to the transformer housing. The shaft of the plunger is placed through the housing hole, the bottom shield hole, the circular air core, and the top shield hole. The plunger bottom side is placed in contact with the diaphragm deflection area and the machine screw type of the metal fastener is placed through the transformer housing mounting hole and into the threaded metal insert fitted into the transformer housing standoff securing the transformer housing and precisely aligning co-planar the deflection surface, the diaphragm facing outer surface, and the diaphragm deflection area.

A flat spring is formed from a single contiguous piece of metal, the flat spring comprises an outer ring, an inner ring, and four spring ribs, the outer ring having more than one spring mount hole. Each of the spring ribs is symmetrical, curvilinear in shape, identical in path length, separated by an air gap, and equally spaced between the outer ring, the inner ring, and the spring rib that are adjacent. Each of the spring ribs is connected, in an integrally formed manner, at a first end to the outer ring and a second end to the inner ring, wherein the spring constant of the flat spring is predetermined by the thickness of the flat spring and identical along two or more axes with respect to the inner ring.

A spring washer comprises a threaded raised inner collar that is sized, fitted through the inner ring, and adhered to the flat spring. The surface of the spring washer is flat and absent raised embossed features. The shaft screws into and protrudes from the spring washer. Machine screw type of metal fasteners are placed through the spring mounting hole and into the threaded metal insert that is in the spring standoff securing the flat spring and precisely aligning the spring washer co-planar with the deflection surface, the diaphragm facing outer surface, and the diaphragm deflection area. The top enclosure and the bottom enclosure are joined and secured together.

Additional shortcomings of the prior art are overcome and additional advantages are provided through the provision of a method of using an improved tocodynamometer transducer. The method comprises the steps of placing a weight on the diaphragm.

The improved tocodynamometer transducer comprises a bottom enclosure having a bottom internal side, a skin-contacting side, and a diaphragm opening therethrough. A top enclosure has a top exterior surface and a top internal surface. A diaphragm is circular in shape. The diaphragm comprises a flexible relief channel integrally formed in the diaphragm proximate to the perimeter of the diaphragm defining a diaphragm deflection area. The diaphragm is secured within the diaphragm opening, a plunger comprises a shaft having a shaft hole along the length of the shaft that is threaded, and a deflection surface having a plunger top side and a plunger bottom side. A ferrite core is threaded around the outer circumference and is solid in composition. The ferrite core is screwed into the shaft hole. A transformer housing comprises a housing bottom having a housing hole centrally located therethrough, an outer circumference surface, and a housing interior region. A linear variable differential transformer has a circular air core. A magnetic shield enclosure comprises a top shield having a top shield hole, and a bottom shield having a shield interior region. The linear variable differential transformer is fitted into the shield interior region. The shaft of the plunger is placed through the housing hole, the bottom shield hole, the circular air core, and the top shield hole. The magnetic shield enclosure is fastened in the housing interior region. The plunger bottom side is placed in contact with the diaphragm deflection area. A flat spring is formed from a single contiguous piece of metal. The flat spring comprises an outer ring, an inner ring, and four spring ribs. The outer ring has more than one spring mount hole. Each of the spring ribs is symmetrical, curvilinear in shape, identical in path length, separated by an air gap, and equally spaced between the outer ring, the inner ring, and the spring rib that are adjacent. Each of the spring ribs is connected, in an integrally formed manner, at a first end to the outer ring and a second end to the inner ring, wherein the spring constant of the flat spring is predetermined by the thickness of the flat spring and identical along two or more axes with respect to the inner ring. And, a spring washer comprises a threaded raised inner collar that is sized, fitted through the inner ring, and adhered to the flat spring. The shaft screws into and protrudes from the spring washer. The flat spring is fastened to the transformer housing. The top enclosure and the bottom enclosure are joined and secured together.

The method continues by, recording a Toco count from the fetal monitor display device, plotting on a graph the weight on the first axis and the Toco count on the second axis, increasing incrementally amount of the weight, returning to the step of placing a weight on the diaphragm until the amount of the weight reached is at least 500 grams, and determining if the graph is linear indicating the improved tocodynamometer transducer has a linear operating diaphragm force range up to at least 500 grams.

Additional features and advantages are realized through the techniques of the present invention. Other embodiments and aspects of the invention are described in detail herein and are considered a part of the claimed invention. For a better understanding of the invention with advantages and features, refer to the description and the drawings.

BRIEF DESCRIPTION OF THE FIGURES

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

DETAILED DESCRIPTION OF THE INVENTION

Figure 1A:
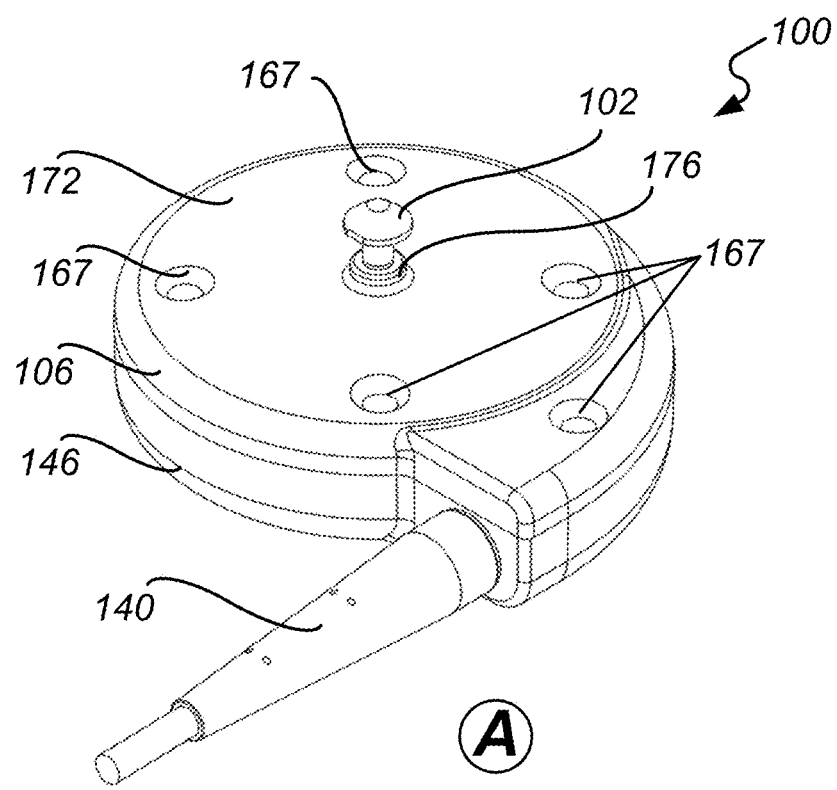
FIGS. 1A-1C illustrate examples of an improved tocodynamometer transducer.
Figure 1A:
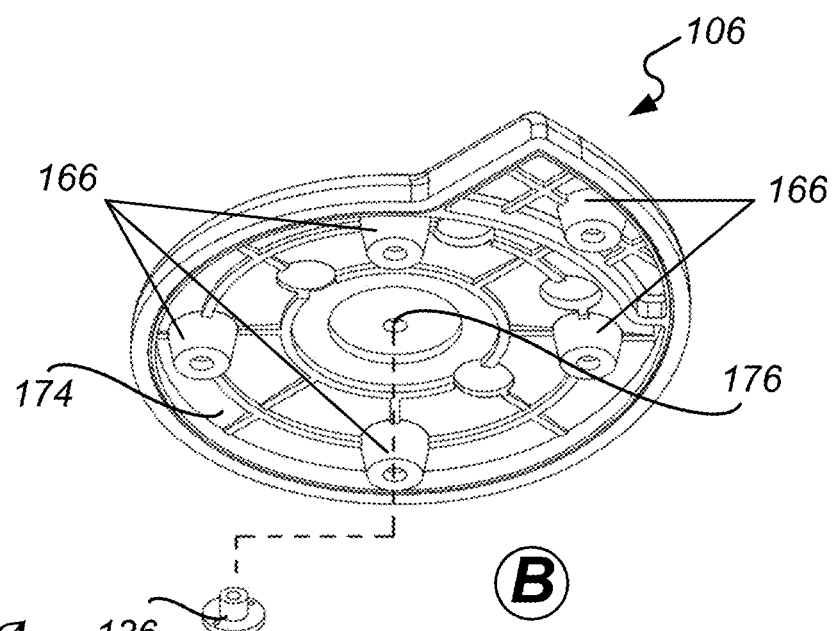

An advantage, in the present invention, when compared to prior transducers, is the baseline of contraction 316 recording is a highly stable output 502 exhibiting negligible drift within +/−2 Toco counts with the calibrated fetal monitor display device 302 at constant room temperature (72° F.) within +/−8 degrees Fahrenheit over a period of a minimum of 72 hours in continuous power-on condition.

Another advantage, in the present invention, is a larger dynamic range 504 for sensing contraction 316 pressure from 0 grams (gm) to 500 gm force of approximately 160 gm/cm$^2$, which is approximately 50% greater force range to sense strong contractions 316 compared to prior transducers that operate only in the range of 50 to 100 gm/cm$^2$ depending on the version of the diaphragm.

Figure 16:
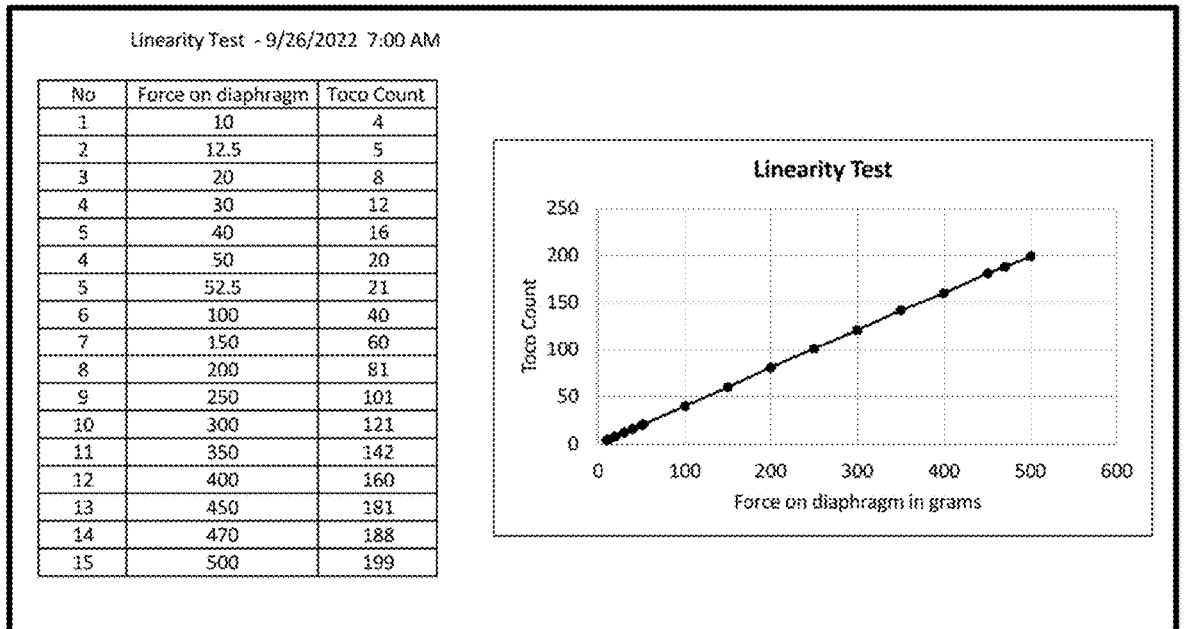
FIG. 16 illustrates examples of a linearity test performed with an improved tocodynamometer transducer.
Figure 16:
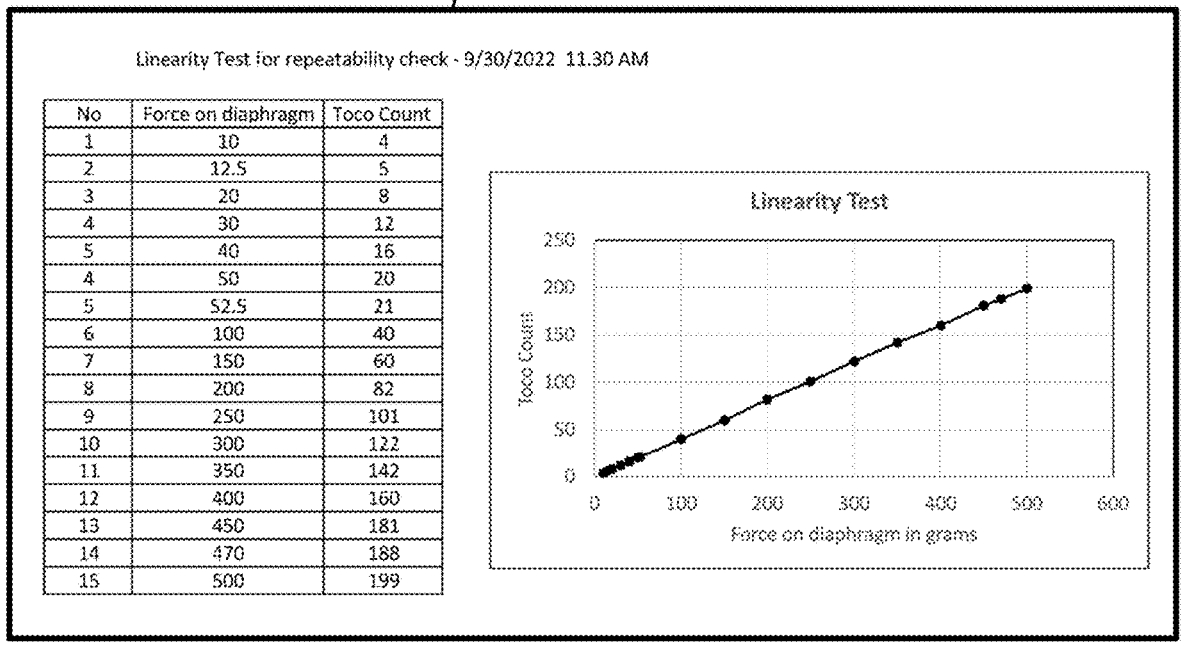
Figure 17:
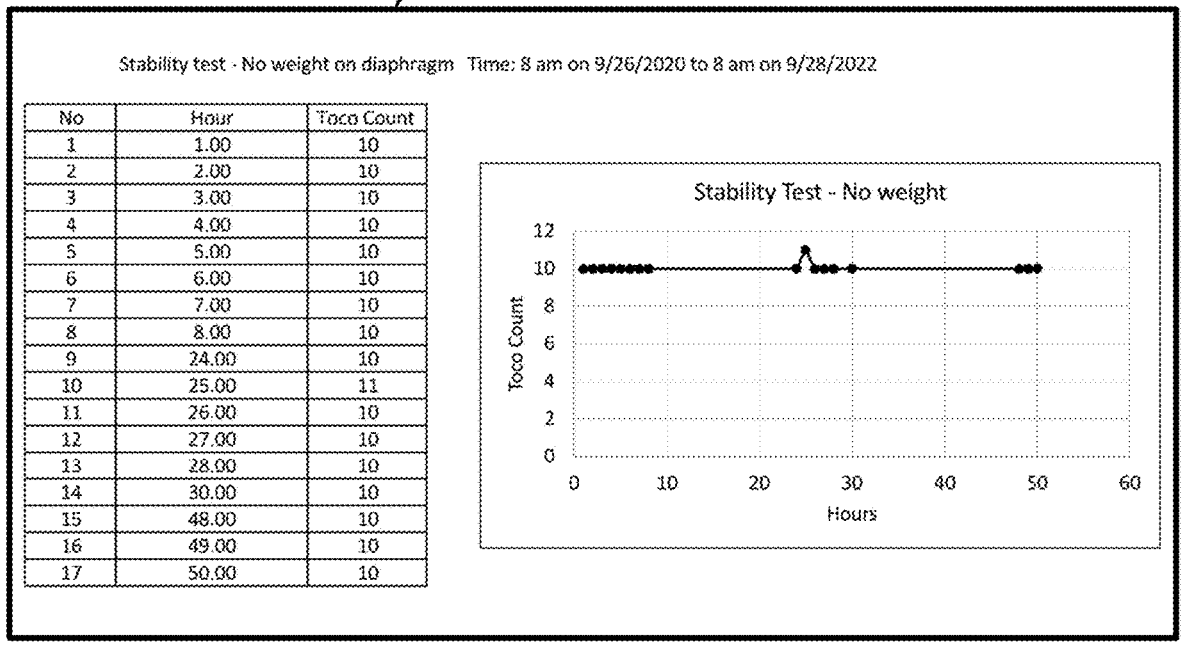
FIG. 17 illustrates examples of a stability test performed with an improved tocodynamometer transducer.
Figure 17:
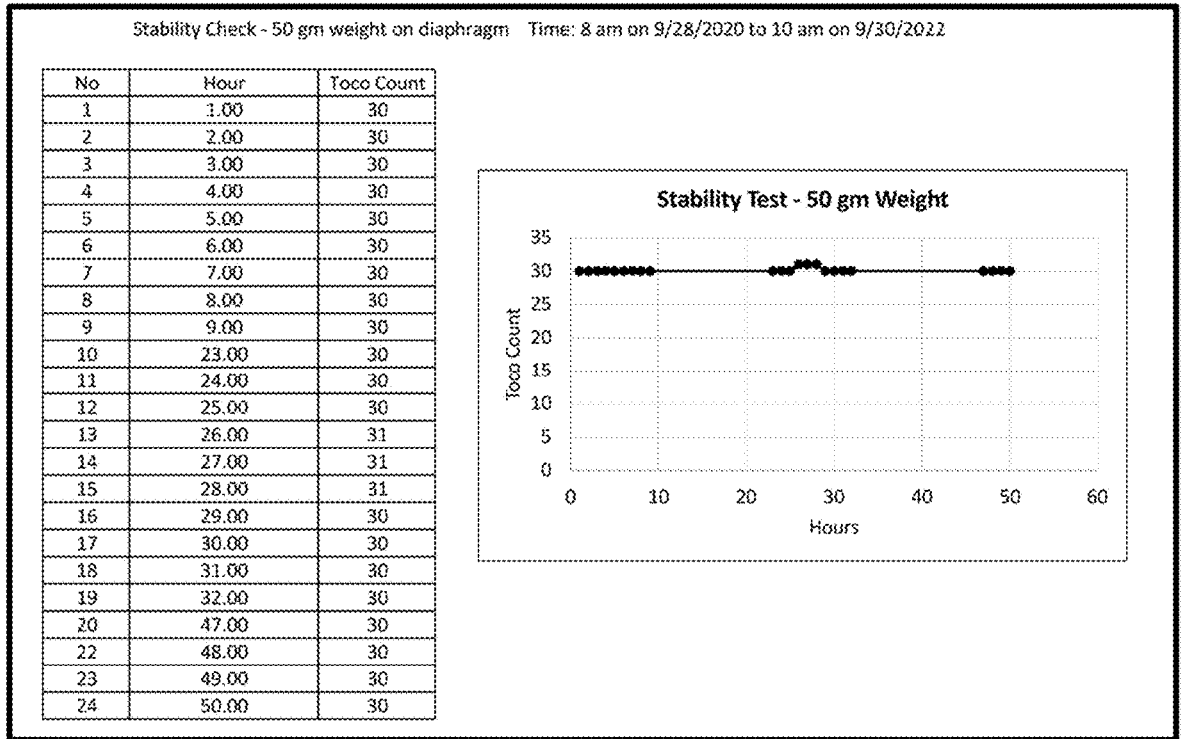

Another advantage, in the present invention, and with reference to FIG. 16, is the superior linearity when graphed using standard calibration weights to put pressure on diaphragm 154 versus the Toco counts displayed across the full dynamic range 504. In this regard, the straight-line graph indicates a proportional change in Vout 502 and Toco count 332 with respect to diaphragm deflection across the entire dynamic range 504. The dynamic range is between a Toco count of 4 at 10 gm force to a Toco count of 200 at 500 gm force.

Another advantage, in the present invention, is a superior sensitivity at a minimum force of 12.5 gm (approximate pressure of 4 gm/cm 2) with a Toco count display 332 of 5 (+/−1 Toco count accuracy). In an exemplary embodiment, this will permit the recording of uterine contraction activity at an earlier stage of pregnancy without inducing premature labor.

Another advantage, in the present invention, is that calibration will not change for years in normal handling/mechanical shock. This enables offering longer warranty terms. This also translates into negligible downtime, and little to no maintenance required except regular external cleaning and disinfecting, promoting utmost ease of use to patients 402 as well as the clinical staff.

Another advantage, in the present invention, is the elimination of repeated failure due to breakage of the molded-in threaded metal insert on the plastic top case. Prior transducers are notorious for these types of physical breakage to plastic areas of the transducer.

Another advantage, in the present invention, is the improved top enclosure 106 and bottom enclosure 146 that when fastened together eliminate the gap-opening near the cable hole 180. In this regard, the present invention uses an o-ring 124 to form a moisture-resistant seal between the top enclosure 106 and the bottom enclosure 146. In an exemplary embodiment, the o-ring 124 can be coated with silicon vacuum grease. Moisture ingress is a common problem in prior transducers that can cause corrosion as well as cause the electrical components on printed circuit board 128 to behave erratically.

In addition, a cable o-ring 142 and a stainless-steel cable fastener 144 can be used to secure the wire cable 140 to the bottom enclosure 146. In this regard, the bottom enclosure 146 has a cable hole 180 through which the wire cable 140 is inserted. The wire cable 140 comprises a threaded end over which a cable o-ring 142 and a stainless-steel threaded fastener 144 secure the wire cable 140 to the bottom enclosure 146.

In addition to better device reliability, as a result of the above advantages as well as other advantages, in the present invention, patient 402 benefits include fewer repeated adjustments of belt 314 tension or repositioning of the improved tocodynamometer transducer 100 and hence great comfort to patient 402 as well as ease of use for the clinical staff. Even in the event that patient 402 moves, the clinical staff can see the clear contraction 316 readings as the baseline shifts with the increased belt 314 pressure. A press of the 'zero' button on the fetal monitor display device 302 corrects the baseline while contraction 316 minima is reached on the waveform 324. The false sense of loosened belt 314 due to slow output drift resulting in offset voltage increase that shifts the contraction 316 minima below the set default Toco count of 10, will be eliminated as the electrical circuit 164 and PCB 128 assembly with the LVDT installation will remain mechanically stable at all times.

Turning now to the drawings in greater detail, it will be seen that in FIG. 1A there is illustrated one example of an improved tocodynamometer transducer 100. Reference 'A' is a top perspective view and reference 'B' is a bottom perspective view. In an exemplary embodiment, one method of securing the tocodynamometer transducer 100 to a patient 402 is by way of a belt 314. In this regard, the threaded button 102 can be inserted into a belt 314 hole and the belt 314 tightened around patient 402.

In an exemplary embodiment, standoffs 166 are conical in shape and wider at the attachment point on the top internal surface 174. This leaves space around the PCB 128 edges 198 after assembly avoiding the introduction of mechanical stress into the PCB 128 and the transformer housing 130 making the output waveform 324 more stable and resistant to drift. The top enclosure 106 comprises more than one fastener hole 167 integrally formed, tapered, and countersunk. The threaded metal insert 136 is fitted into each of the standoffs 182 on the bottom internal surface 135. Each of the fastener holes 167 is aligned with each of the standoffs 166/182 when the top enclosure 106 and the bottom enclosure 146 are joined. Each machine screw type of the metal fastener 104 passes through the fastener hole 167, the standoff 166, and into the threaded metal insert 136 fitted in standoff 182 securing the top enclosure 106 and bottom enclosure 146 together.

The top enclosure 106 can comprise a top exterior surface 172 and a top interior surface 174. A button standoff 176 can be integrally formed on the top exterior surface 172. Threaded metal inserts having a flange 136 can be formed into or otherwise fitted into the button standoff 176 from the bottom interior surface 174 side. A threaded button 102 can then be inserted through the top exterior surface 172 into the threaded metal insert 136 that is molded into or otherwise fitted inside the button standoff 176.

An advantage, in the present invention, is that when the threaded button 102 is tightened into the threaded metal 136, the threaded metal 136 insert is pulled into the button standoff in a manner that prevents the threaded metal insert 136 from being pulled out of the top enclosure 106. By contrast, a common failure point with prior transducers is that the insert is installed from the external surface side and even routine use loosens the insert over time, causing it to fail by pulling out of the case.

Figure 1B:
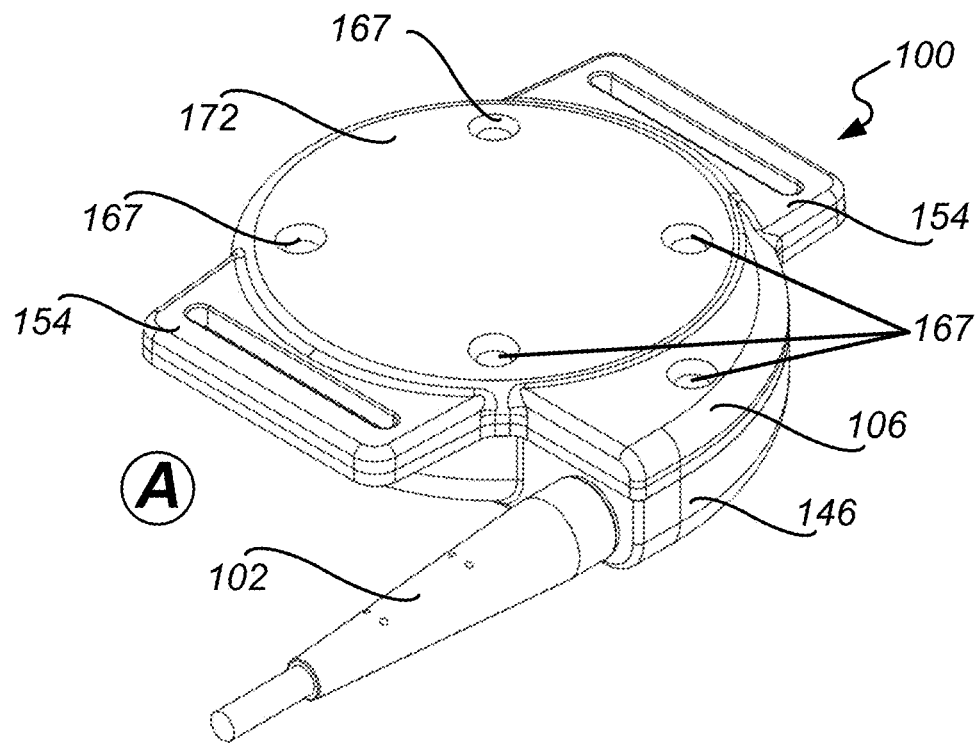
Figure 1B:
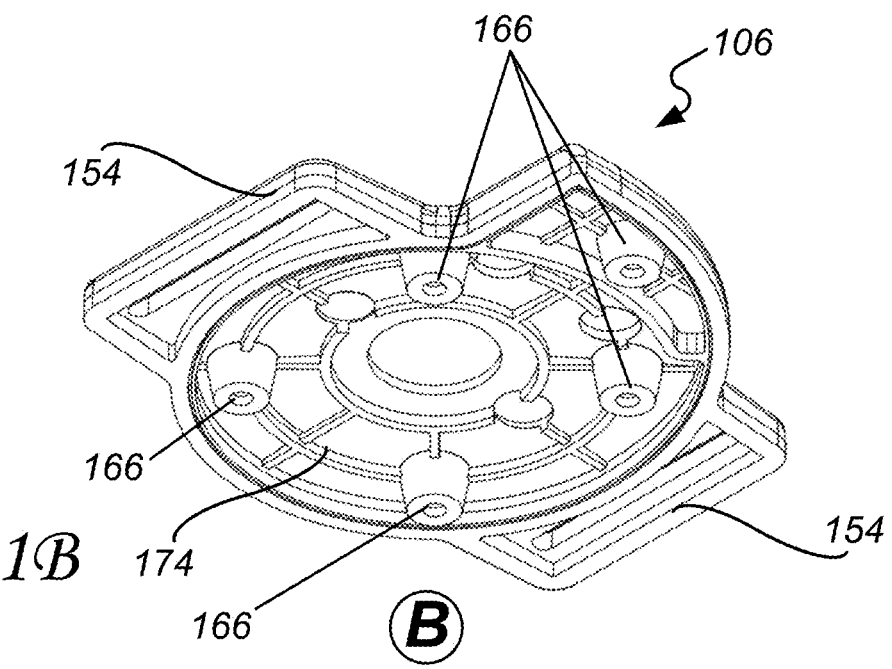

Referring to FIG. 1B, there is illustrated one example of a tocodynamometer transducer 100. Reference 'A' is a top perspective view and reference 'B' is a bottom perspective view. In an exemplary embodiment, the top enclosure 106 can comprise an integrally formed one or more belt loop 154. One method of securing the tocodynamometer transducer 100 to a patient 402 is by way of weaving a belt 314 through the belt loops 154. In this regard, belt 314 can be threaded through a first belt loop 154, across the top enclosure 106, threaded through a second belt loop 154, and belt 314 can then be tightened around patient 402.

Figure 1C:
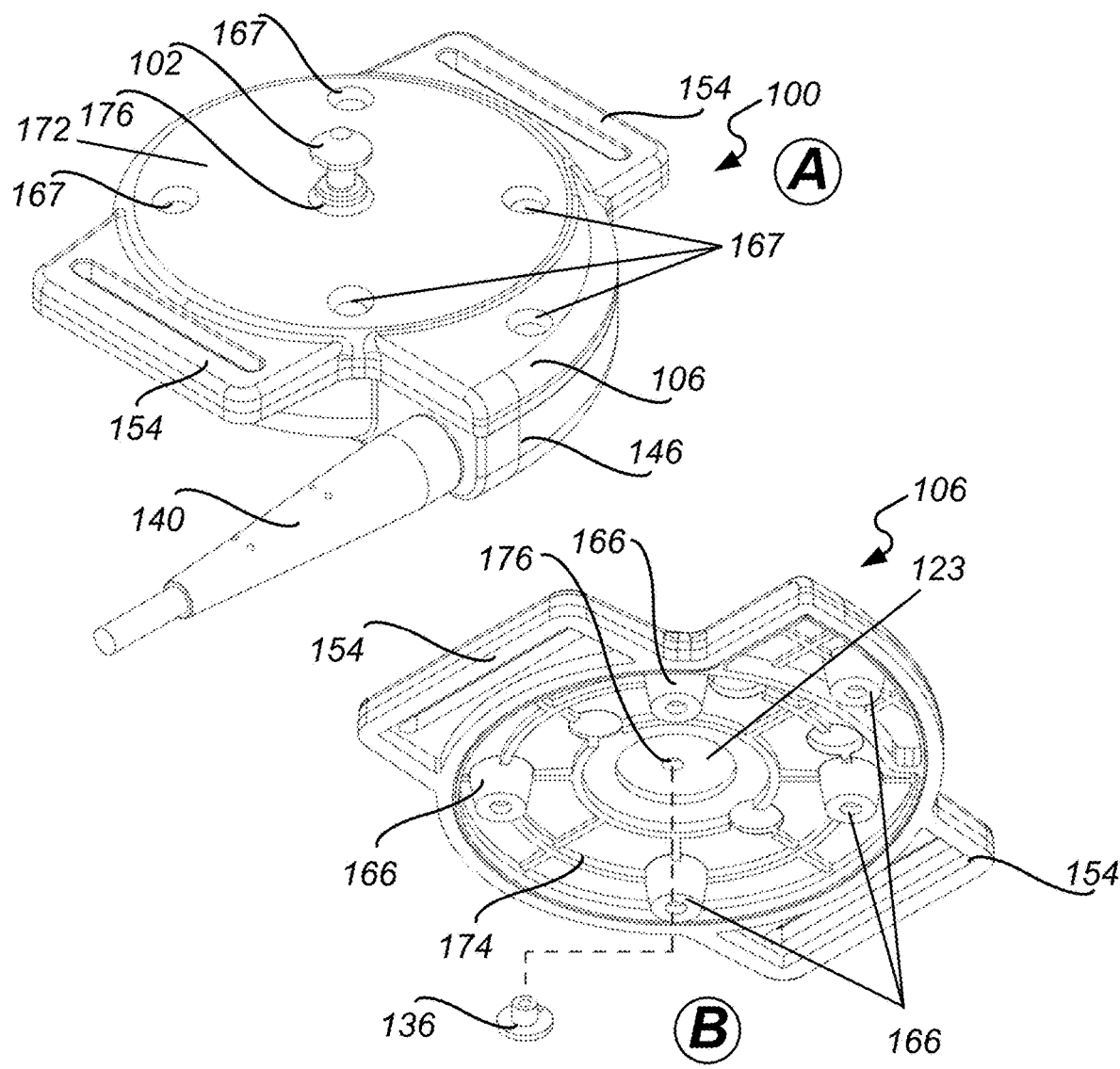
Figure 1C:
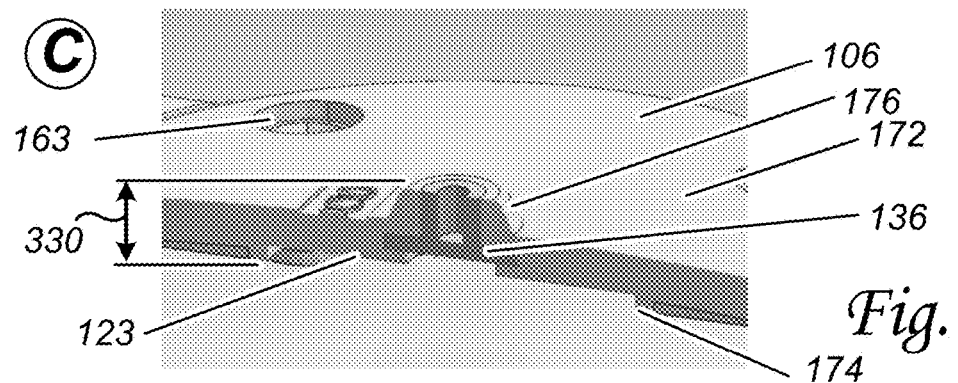

Referring to FIG. 1C, there is illustrated one example of a tocodynamometer transducer 100. Reference 'A' is a top perspective view, reference 'B' is a bottom perspective view, and reference 'C' is a sectional perspective view. In an exemplary embodiment, the top enclosure 106 can comprise the threaded button 102 for attachment to patient 402 as described in FIG. 1A as well as the belt loop 154 for attachment to patient 402 as described in FIG. 1B.

In an exemplary embodiment, as in FIG. 1A, the top enclosure 106 can comprise an integrally formed one or more belt loop 154. Or as in FIG. 1B, the top enclosure 106 can comprise a top exterior surface 172 and a top interior surface 174, and a button standoff 176 that is integrally formed on the top exterior surface 172. The threaded metal insert 136 is fitted into the button standoff 176 from the top interior surface 174 side, and a threaded button 102 is inserted through the top exterior surface 172 into the threaded metal insert 136 that is fitted inside the button standoff 176. Or as in FIG. 1C, the top enclosure 106 can comprise a top exterior surface 172, a top interior surface 174, and an integrally formed one or more belt loop 154. A button standoff 176 is integrally formed on the top interior surface 177. The threaded metal insert 136 is fitted into the button standoff 176 from the top interior surface 174 side. A threaded button 102 is inserted through the top exterior surface 172 into the threaded metal insert 136 that is fitted inside the button standoff 176.

Figure 2:
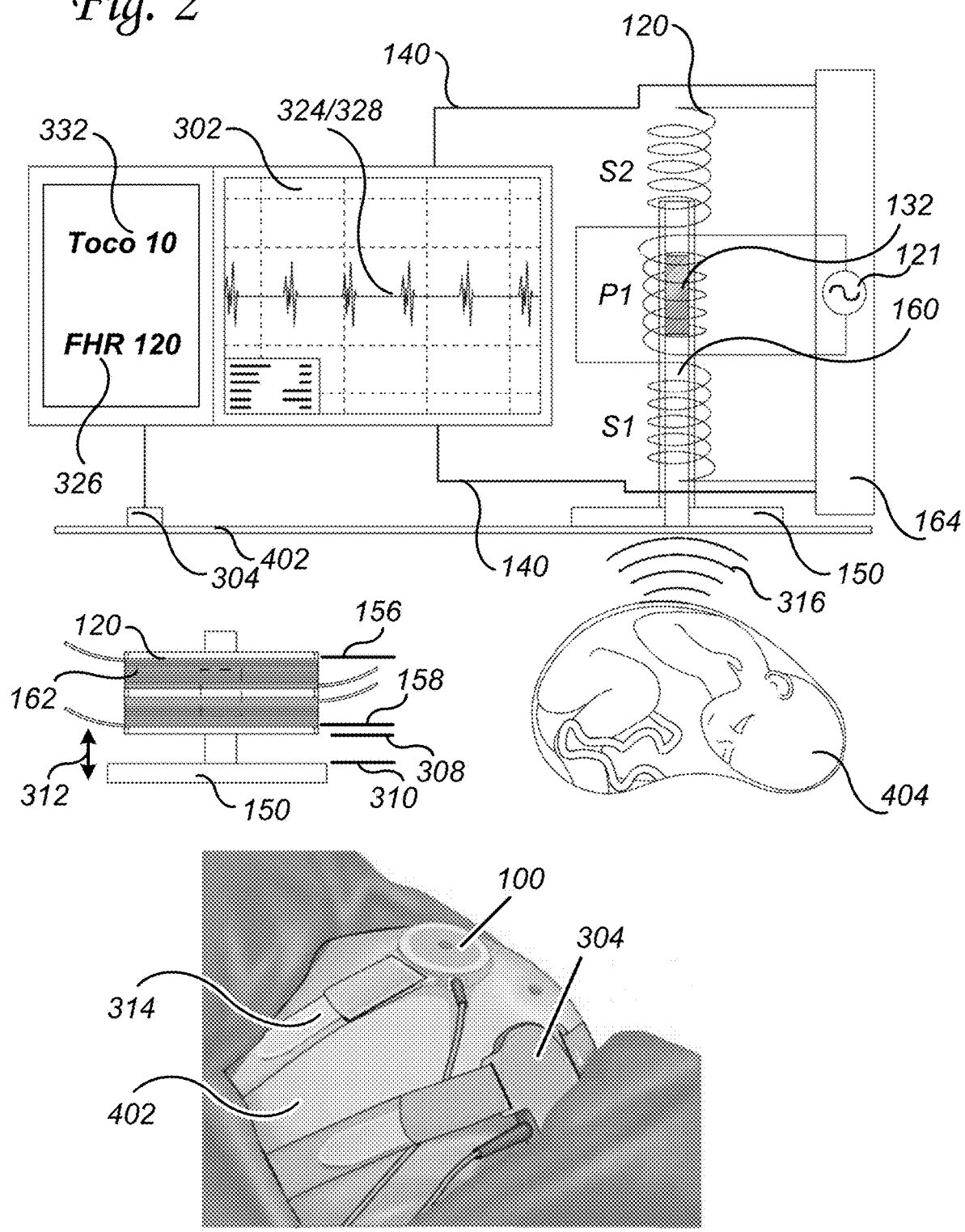
FIG. 2 illustrates one example of a tocodynamometer system.

Referring to FIG. 2, there is illustrated one example of a tocodynamometer system. In an exemplary embodiment, patient 402 that is pregnant with baby 404 can secure a belt 314 that comprises a tocodynamometer transducer 100 on the abdomen proximate to baby 404. Contained within the tocodynamometer transducer 100 enclosure is a plunger 150 that is positioned to detect contractions 316. In this regard, the plunger 150 comprises a ferrite core 132 that moves 312 within the circular air core 160 of a linear variable differential transformer (LVDT) 120. The motion of the plunger 150 is mechanically limited by the diaphragm 184 on one side to a −100% displacement 310 and the transformer housing 130 diaphragm facing outer surface 111 (better illustrated in at least FIG. 8) on the other side to a +100% displacement 308. The mechanical limits keep the ferrite core 132 contained within the windings 162 of the LVDT between a maximum deflection top wire winding edge 156 and a minimum deflection bottom wire winding edge 158. This keeps the voltage output linear 502 across the entire dynamic range 504. In the alternative, prior transducers use hollow longer length ferrite cores in LVDT designs, by allowing the ferrite core to escape the boundary of the windings, even partially, the linear output is lost and electromagnetic interference (EMI) is allowed to enter the circuit further degrading the transducer response.

By way of an electrical circuit 164, a sine wave 121 is coupled to the primary windings of the LVDT 120, and a voltage from the secondary windings is conditioned into a linear voltage output signal 502. The design of the present invention LVDT 120, mechanically limited plunger 150, and ferrite core 132 characteristically generate a linear voltage output 502 which can be communicated by way of a wire cable 140 to a display device 302 where a Toco count 332 and waveform 324 can be determined and displayed.

An ultrasound transducer 304 can also be positioned on the abdomen of patient 402 in proximity to baby 404 and interconnected with the display device 302. In this regard, a fetal heart rate (FHR) 326 and associated waveform 328 can be determined and shown on display device 302.

Figure 3:
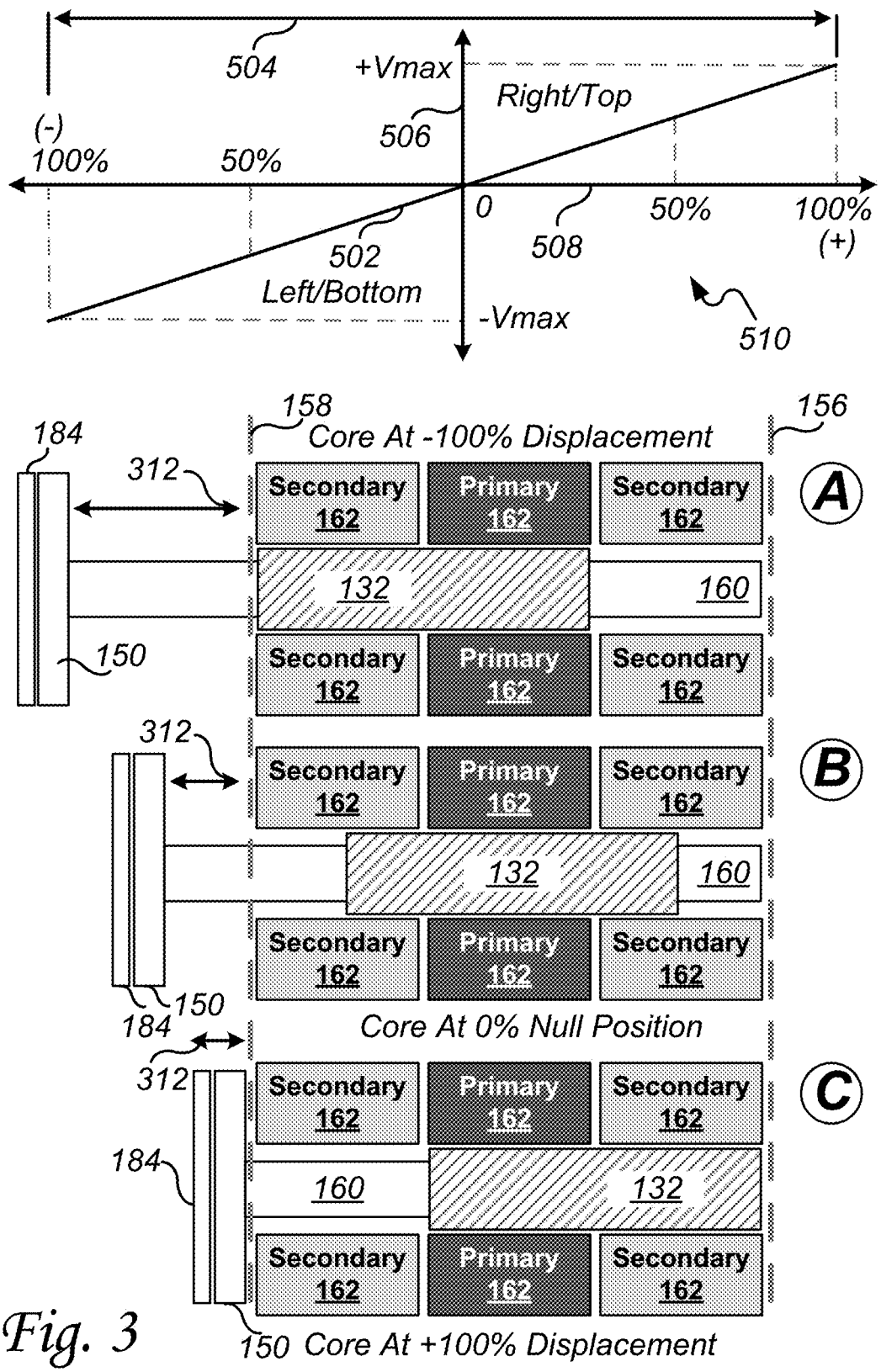
FIG. 3 illustrates one example of the electrical performance characteristics of a linear variable differential transformer.

Referring to FIG. 3, there is illustrated the electrical performance characteristics of an LVDT 120. An advantage, in the present invention, and an improvement over prior LVDT transformer-based transducers is that a shorter, solid ferrite core 132 is used in combination with other mechanical improvements that while increasing the travel distance 312, within the wire windings 162 of the LVDT 120, prevent the ferrite core 132 from breaching the top wire winding edge 156 or the bottom wire edge 158. This ensures that the LVDT 120 output is linear across the dynamic range of motion 504 of the plunger 150. This is something that prior LVDT-based transducer designs failed to consider by selecting longer hollow ferrite cores that protrude from the LVDT wire windings causing non-linear voltage output variations that impact the accuracy and reliability of the readings.

In an exemplary embodiment, the LVDT has a top wire winding edge 156 and a bottom wire winding edge 158 that is defined by the location and length of a wire winding 162 around the circular air core 160. In operation, the plunger 150 transitions between a maximum deflection 308 and a minimum deflection 310. During maximum deflection 308 the ferrite core 132 is positioned below the top wire winding edge 156, and during minimum deflection 310 the ferrite core 132 is positioned above the bottom wire winding edge 158. The ferrite core 132 remains within the length of the wire winding 162 of LVDT generating a linear voltage output 502 across the plunger 150 range of travel 312. The ferrite core 132 is threaded around the outer circumference and is solid in composition. The ferrite core 132 is screwed into the shaft hole 152 of the plunger 150 shaft 134.

In an exemplary embodiment and with reference to FIG. 3, in reference 'A', when plunger 150 comprising the ferrite core 132 moves 312 towards the bottom wire edge 158 without breaching the bottom wire edge 158 boundary, the result is a linear voltage output from the LVDT 120. The voltage output can be conditioned by the electrical circuit 126 and graphed 510 Vout 506 as a relationship of the percentage of the ferrite core 132 displacement 508, ranging from 0% to −100%. Graph 510 illustrates this as Vout 502 from the origin 0V to −Vmax in the left/bottom quadrant of the graph.

In reference 'B', when the ferrite core 132 is positioned midway between the top wire edge 156 and the bottom wire edge 158, the ferrite core 132 is considered to be at 0% displacement (null position), and the Vout 502 voltage is 0V.

In reference 'C', when plunger 150 comprising the ferrite core 132 moves towards the top wire edge 156 without breaching the top wire edge 156 boundary, the resultant is a linear voltage output from the LVDT 120. The voltage output can be conditioned by the electrical circuit 126 and graphed 510 Vout 506 as a relationship of the percentage of the ferrite core 132 displacement 508, ranging from 0% to +100%. Graph 510 illustrates this as Vout 502 from the origin 0V to +Vmax in the right/top quadrant of the graph.

In contrast to prior LVDT-based transducers, in the present invention by using a ferrite core 132 that is solid the length of the ferrite core 132 can be shorter than prior hollow ferrite cores. The shorter ferrite core 132 allows more travel distance within the air core 160 of the LVDT transformer. The greater travel distance translates into a greater dynamic range 504 of output for the tocodynamometer transducer 100. In addition, by mechanically constraining the ferrite core 132 travel path to remain between the top wire winding edge 156 and the top wire winding edge 158, the voltage output of the LVDT 120 and thus the conditioned output signal to the display device 302 remains linear, as illustrated in the FIG. 3 graph 510, across the entire dynamic range 504. In the present invention, the dynamic range 504 can be characterized by sensing contraction pressure in the force range from 0 gm to 500 gm which is approximately 160 gm/cm$^2$. In contrast, this is at least a 50% greater dynamic range than the prior transducers which are limited to force detection ranges of less than 100 gm/cm$^2$. A shorter ferrite core 132 length and a more mechanically stable PCB 128 assembly eliminate the output offset change and slow drift which is a common shortcoming of prior LVDT-based transducers.

Figure 4:
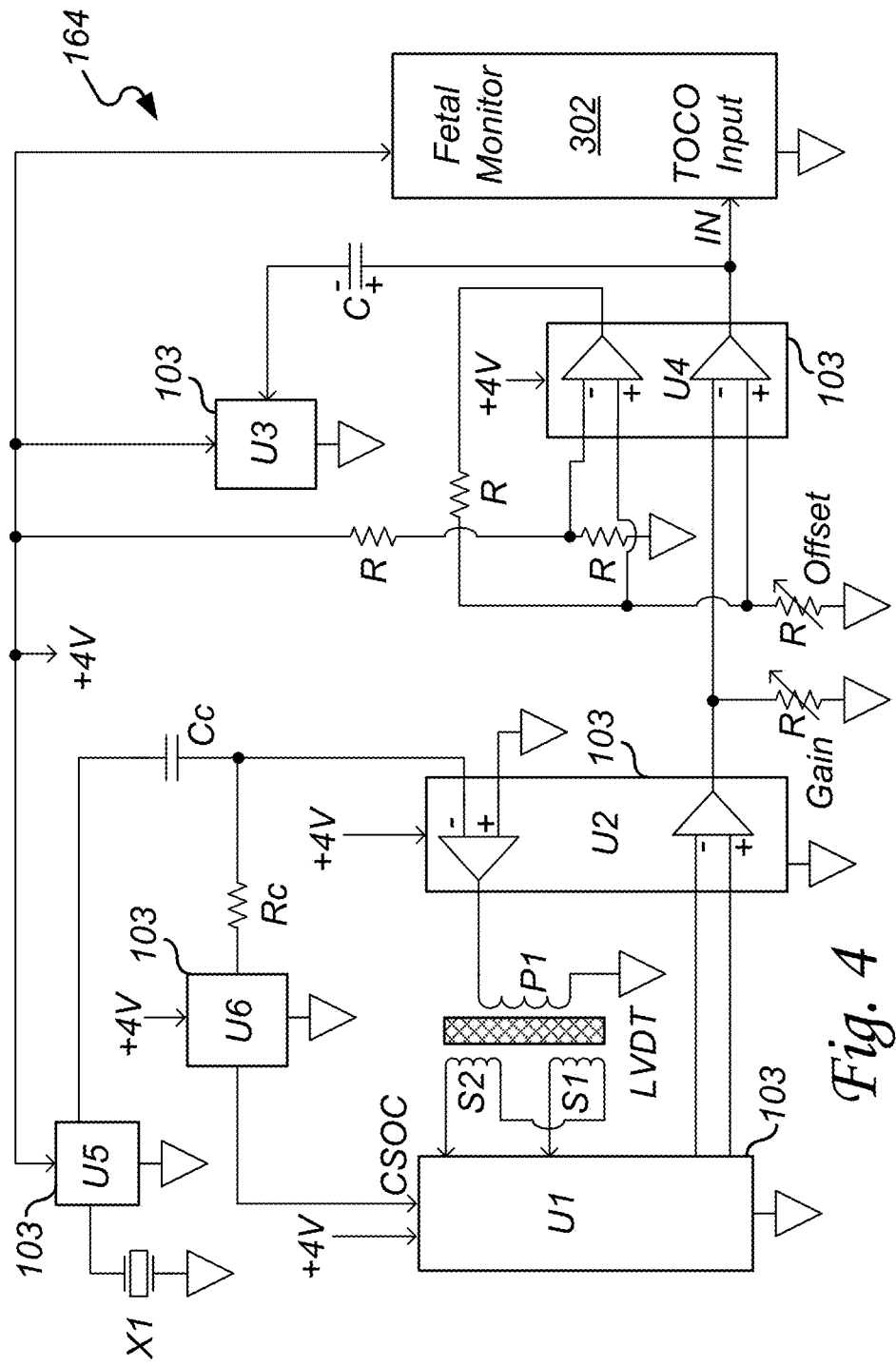
FIG. 4 illustrates one example of an electrical circuit.

Referring to FIG. 4, there is illustrated one example of an electrical circuit. A shortcoming of prior transducers that is an advantage and improvement in the present invention is the use of semiconductors that are designed for operating voltages of +4.0V DC or less. In this regard, fetal monitor display devices supply +4.0V DC power to the printed circuit board (PCB). Prior transducers use a dual op-amp IC chip U2 (AD822) which is manufactured by ANALOG DEVICES and is rated to work reliably at a minimum +5V DC power supply. One of the op-amps from this chip is used to convert the 32.678 kHz square wave into a sinusoidal waveform to drive the LVDT primary coil. The second Op-Amp is used as a differential amplifier with a fixed amplification gain of 10 to boost the output of the LVDT secondary coil after it is put through a switched capacitor block. A shortcoming of prior transducers is that due to a 20% lower power supply voltage (receiving +4.0V DC, not +5.0V DC) certain of the semiconductors are operated below the design-rated voltage. As a result, the full dynamic range of OP-amp is not utilized, sensitivity is reduced, and reading stability suffers greatly causing huge drifts and distortions in LVDT input that results in output drift from the transducer due to bias current variations. In general, prior transducers give intermittent/spurious responses because at least one of the semiconductors is operated at insufficient supply voltages.

An advantage, in the present invention, is an electrical design change that remedies insufficient supply voltage shortcomings of prior transducers. In this regard, the U2 AD822 dual Op-Amp semiconductor is replaced with the AD4661-2 which characteristically has improved electrical specifications and is rated to work reliably at a supply voltage of +4.0V DC (or lower).

In an exemplary embodiment, in the present invention, the electrical circuit 164 displaces ferrite core 132 due to contraction 316 pressure on diaphragm 184 plunger 150 combination, producing a change in the output voltage of LVDT 120 two secondary coils S1 and S2 which are connected in series in opposition. The primary coil P1 at the center of LVDT 120 is excited with a 32.768 kHz sinusoidal wave that produces magnetic flux at the center where it is coupled to the two secondary coils S1 and S2, one on top (S2) and the other at the bottom (S1), through the ferrite core 132.

The LVDT 120 output waveform is fed to a differential amplifier (U2, OP-Amp AD822) through dual precision instrumentation switched capacitor block (U1). Output from this stage is amplified through another op-amp (U4) before supplying the signal to the fetal monitor through cable 140.

Cable 140 connects at one end to electrical circuit 164 on PCB 128 through a 4-pin connector 169 and at the other end through a 12-pin circular connector to the Toco Input on the fetal monitor display device 302. The pins on PCB 128 have two connections that send the Vout 502 signal to a fetal monitor. The other two connections are a +4.0V DC supply from the fetal monitor display device 302 to power the electric circuit 164. Cable 140 has shielding that is connected to one of the pins of 12 pin connector for proper ground connection whereas it is electrically not connected anywhere on the electric circuit 164.

The output voltage waveform 324 in response to contraction 316 pressure from the improved tocodynamometer transducer 100 is processed inside the fetal monitor display device 302 to display the numerical value of Toco count 332 and waveform 324 representing the applied force/pressure amplitude. In addition, data and other information can be recorded on a strip chart paper for frequency determination.

The contraction Toco count 332 and waveform 324 can be correlated with a fetal heart rate (FHR) count 326 and waveform 328 obtained from a separate NAUTILUS 5700LAX/HAX ultrasound transducer and other similar transducers. The readings 322/326 and waveforms 324/328 can be monitored and interpreted by trained clinical/medical professionals to determine among other things the fetal 404 conditions and take appropriate action. Reliability of contraction 322/324 and FHR 326/328 counts and waveform recordings can inform or otherwise determine the type of medical care the pregnant patient 402 and the unborn fetus 404 will require.

Figure 5:
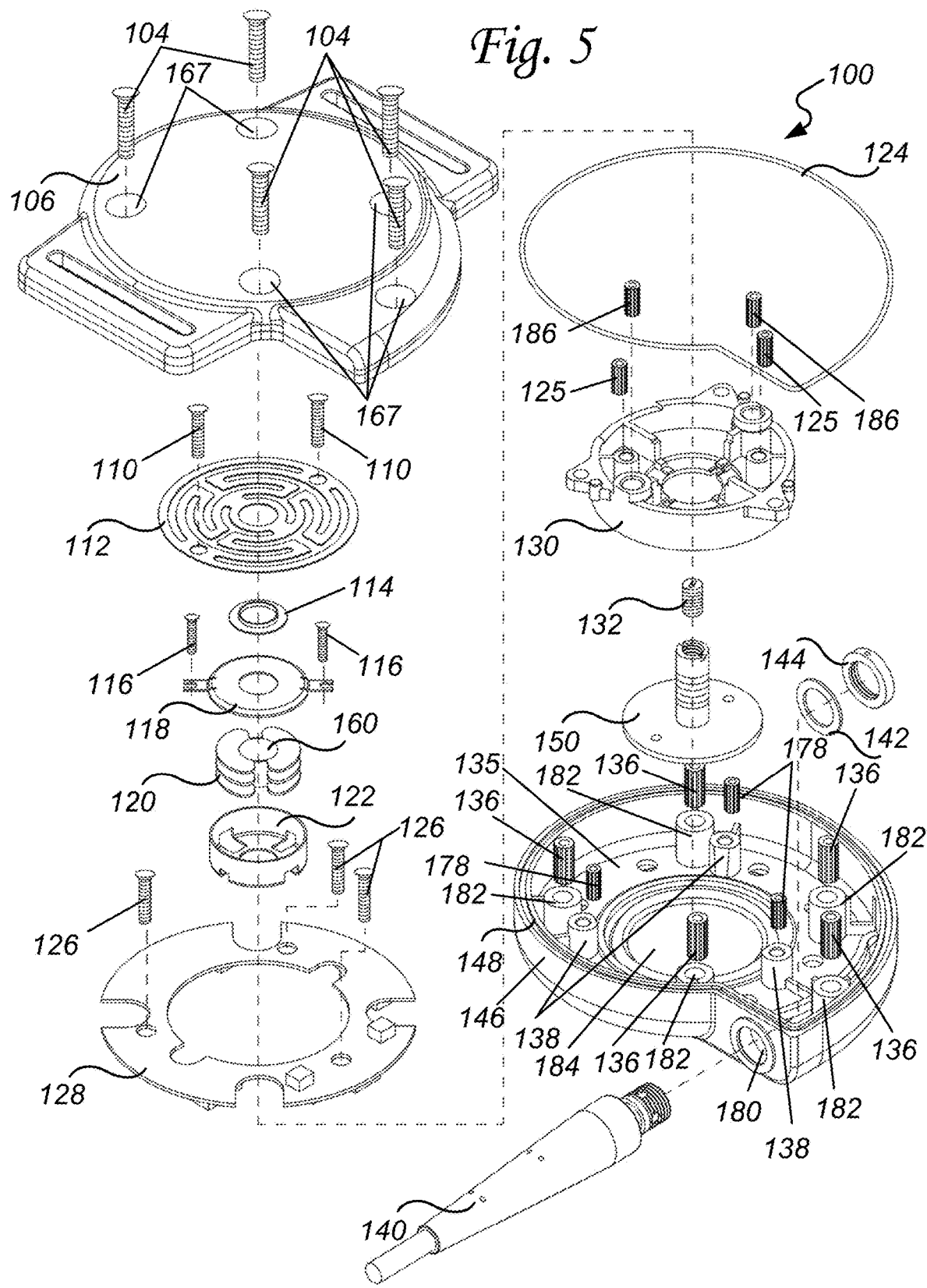
FIG. 5 illustrates one example of an improved tocodynamometer transducer assembly.
Figure 6:
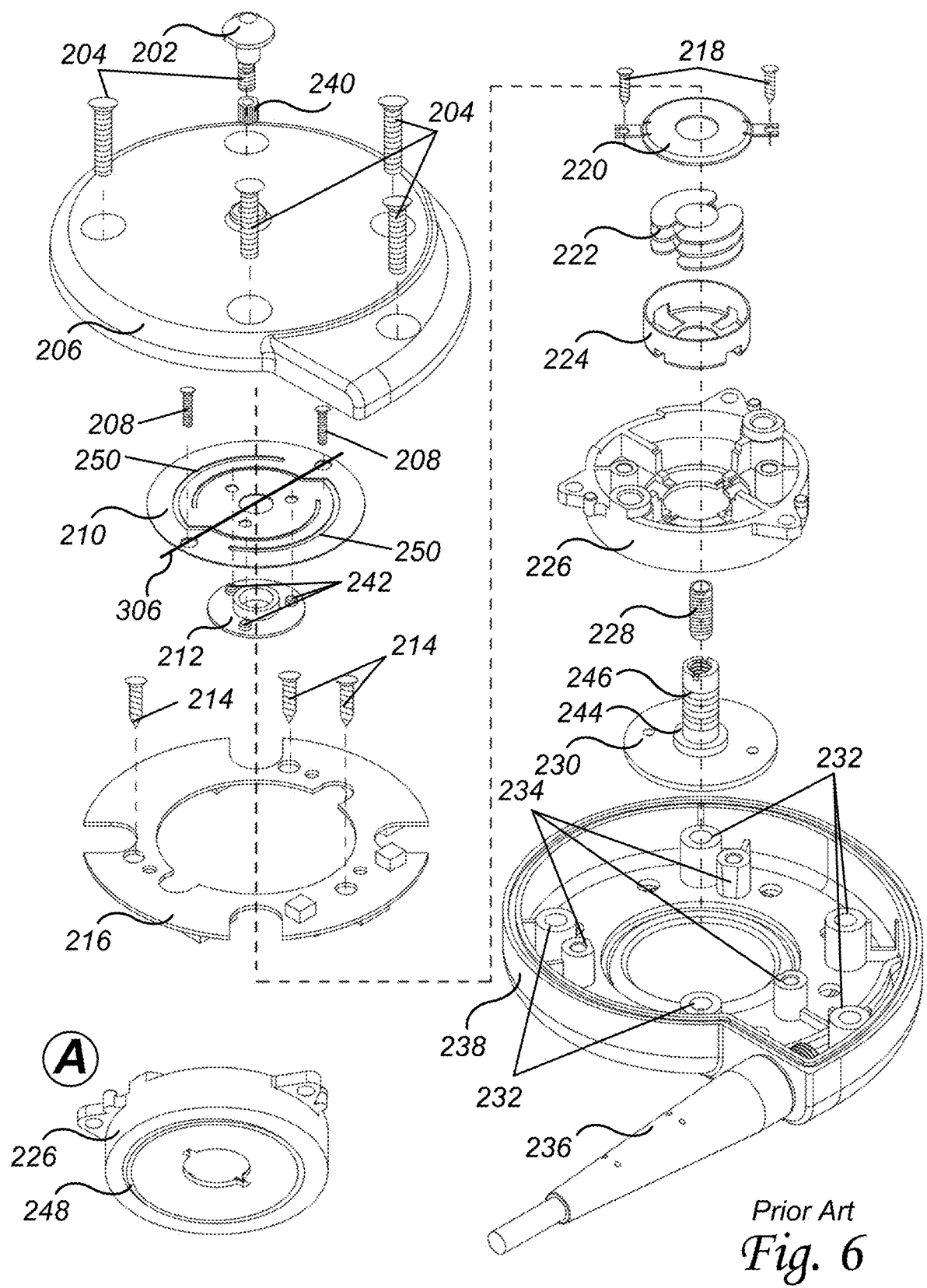
FIG. 6 illustrates a prior art tocodynamometer transducer.

Referring to FIG. 5 and with reference to prior art FIG. 6, there is illustrated one example of an improved tocodynamometer transducer 100 assembly. An advantage, in the present invention, is that the improved tocodynamometer transducer 100 permits more accurate uterine contraction 316 waveforms sensing linearly proportional to force/pressure with consistency and reliability without drift or offset as compared to prior transducers. In general, the dynamic range is significantly shorter for prior transducers and varies from unit to unit based on the diaphragm used as well as the spring part number version.

In an exemplary embodiment, an advantage, in the present invention, compared to prior transducers, is that the bottom enclosure 146 with diaphragm 184 accommodates more internal space between LVDT 120 transformer housing 130, the bottom enclosure 146, and diaphragm 184 itself so that plunger 150 has at least 3 mm (3000 micrometers) stroke length. In addition, three threaded metal inserts 178 are fitted into printed circuit board standoffs 138 so that the PCB 128 can be affixed into position with machine screws. This increases the mechanical stability and provides an even and equal securing hold on the PCB 128. Prior transducers used self-tapping screws 214 into plastic mounts 234. The self-tapping screws 214 tend to degrade the plastic mounts 234 internally over time causing the self-tapping screws 214 to loosen. In addition, it is common for self-tapping screws 214 to misalign on insertion into the standoff post creating uneven pressure on the PCB 128 that can negatively impact the long-term reliability and mechanical stability of prior transducers.

Another advantage, in the present invention, compared to prior transducers is that a large diameter step ring 244 around the shaft 246 of the plunger 230 is absent in the present invention. In this regard, the present invention utilizes a shaft 134 that connects to the plunger 150 in a manner that step ring 244 is eliminated. The benefit, in the present invention, is that the stroke length of the plunger 150 is increased by 1.5 mm/1500 micrometers allowing the ferrite core 134 to be displaced in a wider range within the LVDT 120 transformer which increases the dynamic range 504 of the improved tocodynamometer transducer 100.

Figure 8:
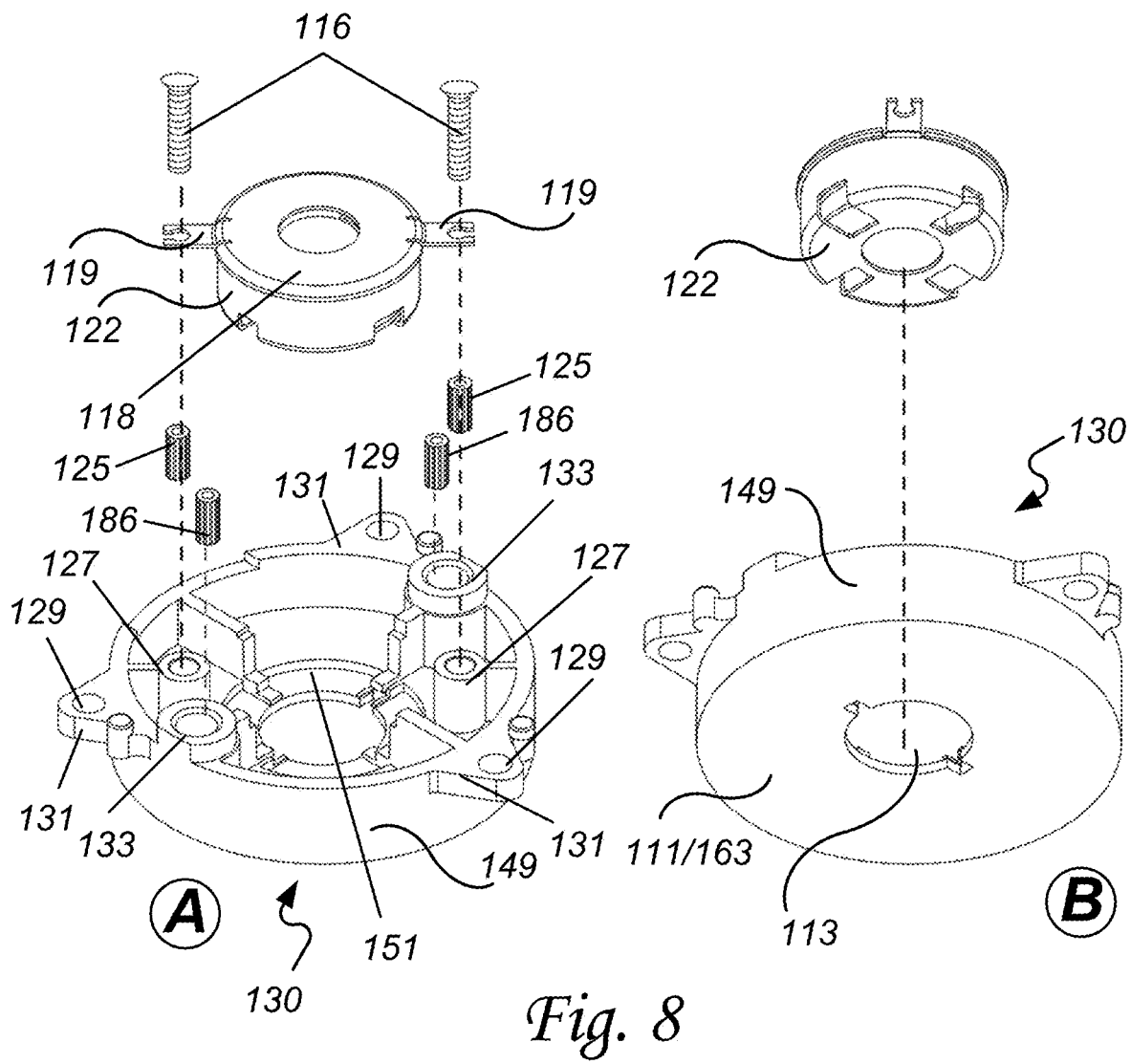
FIG. 8 illustrates one example of a transformer housing assembly.

Another advantage, in the present invention, is an embossed raised edge 248 in prior transducers is eliminated on the diaphragm facing outer surface 111 of the transformer housing 130 (better illustrated in at least FIG. 8). The benefit of removing the embossed raised edge 248 is that the plunger 150 travel is further unencumbered increasing the dynamic range 504 of the improved tocodynamometer transducer 100 by increasing the stroke length of the plunger by 0.4 mm (400 micrometers).

Another advantage, in the present invention, is that the thickness 176/330 of the top enclosure 106, better illustrated in at least FIG. 1C, creates a cavity 123 just above the plunger 150, shaft 134 apex that comes out of the top of the flat spring 112 when assembled. Cavity 123 increases the clearance of shaft 134 from the top case 106 ensuring that the improved tocodynamometer transducer 100 has full dynamic range 504 rather than the shaft 134 getting mechanically stopped by the top enclosure 106. In this regard, and in contrast to prior transducers, the space between the plunger apex and plastic top case is too close. As such, when the prior transducer is strapped to the abdomen of the patient, the plunger shaft often hits the top case or has very little space left for sensing the contractions thereby reducing the dynamic range.

In operation, this means that, in some prior transducers, there is no contraction sensing at all after the belt strap is put on the patient and in some prior transducers there is not a full dynamic range coverage for the contraction sensing. In addition, the external EMI noise is picked-up sporadically as the ferrite core is longer than the LVDT bore allowing EMI interference to enter the circuit.

The absence of signal linearity and the introduction of EMI noise in prior transducers emphasize the importance of linearity testing. In the present invention, a method of linearity testing is illustrated in at least FIGS. 14 and 16. In this regard, linearity results across a dynamic range of up to 500 gm force were performed on the improved tocodynamometer transducer 100 with a minimum sensitivity (12.5 gm force), and linearity of +/−4 Toco counts (worst case +/−2.0% full-scale of 200 Toco counts for 500 gm force). Teflon weights should be used in the testing as metal weights can adversely impact the magnetics in the electrical circuit 164 and thus the results can get distorted.

In addition, in operation, and as better illustrated in at least FIG. 1C, the increased thickness 330 helps to improve force and thus the durability that the improved tocodynamometer transducer 100 can withstand. In prior transducers, the button 202 style top plastic case 206 has a weakness and a very high failure rate of the metal insert 240, which is inserted from the outside of case 206, getting pulled out. As a result, button 202 gets knocked off from the plastic substrate 206 after short usage under normal handling conditions.

The improved tocodynamometer transducer 100, in the present invention, solves this shortcoming by installing a threaded metal insert 136 having a flange on the top internal surface that is anchored inside the plastic substrate 176 as illustrated in at least FIG. 1C reference 'C'. The benefits of the thicker 330 plastic substrate 176 top enclosure, the threaded button 102 and the threaded metal flange insert 136 secured from the top interior surface 174 side of the top enclosure, improve the mechanical stability and reliability of the improved tocodynamometer transducer 100. The improved tocodynamometer transducer 100 can withstand forces during the practical drop test from 18 feet high onto a hard concrete floor.

Prior top case 206 had a plurality of round standoffs that when assembled put stress on PCB 216 and LVDT assembly 226. This mechanical stress caused drift and spurious spiking in the output waveform of the prior transducer. In an exemplary embodiment and an advantage in the present invention, as better illustrated in FIG. 1C, the standoffs 166 are conical in shape and wider at the attachment point on the top internal surface 174. This leaves space around the PCB 128 edges after assembly avoiding the introduction of mechanical stress into the PCB 128 and the transformer housing 130 making the output waveform 324 more stable and resistant to drift.

Another factor is that in prior transducers the use of self-tapping screws 214 to fasten the PCB 216 assembly into the bottom plastic case 238. The self-tapping screws 214 start becoming loose in a very short span of time allowing plunger 230 to move outward towards the diaphragm which reflects as a slow drift in LVDT output 222 (increase in offset voltage). Additionally, as the plunger drifts outward the ferrite core 228 sticks further out of LVDT bore, and eventually, the transducer does not sense any contractions when the plunger 230 loses coupling with the diaphragm but external noise is picked up making the transducer unreliable.

In an exemplary embodiment, in the present invention, more than one metal fastener 104/110/116/126 is used in the assembly of the improved tocodynamometer transducer 100. Such metal fasteners 104 can be 4-40 ×⁵⁄₁₆ inch, 110 can be 4-40 ×¼ inch, 116 can be 2-56 ×¼ inch, and 126 can be 2-56 ×⅜ inch, or other suitable screw sizes can be used, as may be required and/or desired in a particular embodiment.

As better illustrated in at least FIGS. 5 and 8, in an exemplary embodiment, more than one threaded metal insert 125 can be 2-56 threaded and fitted into each of the magnetic shield standoffs 127, and more than one threaded metal insert 136 can be 4-40 threaded and fitted into each of the standoff 136, more than one threaded metal insert 178 can be 2-56 threaded and fitted into each of the transformer housing standoff 178, and more than one threaded metal insert 186 can be 4-40 threaded and fitted into each of the spring standoffs 186. Other suitable threaded insert sizes can be used, as may be required and/or desired in a particular embodiment.

In an exemplary embodiment, enclosure 106/146 can comprise a bottom enclosure 146 and a top enclosure 106. Better illustrated in at least FIGS. 1C and 10, the top enclosure 106 has a top exterior side 172 and a top internal side 174. The bottom enclosure 146 has a bottom internal side 135, a skin-contacting side 137, and a diaphragm opening 141 therethrough.

More than one standoff 166 (top)/182 (bottom) are integrally formed on the top internal surface 174 and the bottom internal surface 135. Each of the standoffs 166 on the top internal surface 174 is conical in shape and wider at the attachment point on the top internal surface 174. The threaded metal insert is fitted into each of the standoff 188 on the bottom internal surface 135.

An advantage, in the present invention, is in the design of the bottom enclosure 146. In this regard and in contrast to prior transducers, three metal threaded inserts 178 are fitted into the printed circuit board standoffs 138 on the bottom enclosure 146. This enables the PCB 128 and transformer housing 130 to be mounted with machine screws 126 instead of self-tapping screws 214 into plastic mounts 234. A benefit of the improved tocodynamometer transducer 100 is that by using machine screws into threaded metal inserts instead of self-tapping screws into plastic, superior physical stability of the bottom enclosure 146 enclosure is gained. In addition, stresses and cracking prevalent in the prior bottom 238 near the fastener mounting areas 232/234 and around the diaphragm opening plastic are eliminated or otherwise avoided in the improved tocodynamometer transducer 100.

Another advantage, in the present invention, and in contrast to prior transducers is the elimination of a gap between the top enclosure and the bottom enclosure when they are joined. In this regard, the prior transducer is notorious for allowing moisture to enter the enclosure by way of a gap between the top 206 and bottom enclosure 238 that is introduced by way of the plastic molding process utilized that allows shrinkage and deformation at the critical joining edges. Such moisture can cause intermittent/spurious functional problems as the PCB 216 has surface mount device (SMD) components (integrated circuits (IC), resistors, capacitors) with electrical lead spacing as short as 0.45 mm (450 micrometers). While prior transducers are in storage (not connected to the fetal monitor powered-on), the moisture condenses on metallic leads of the SMD IC chips/components at low room temperatures. Then when the transducer is put in usage, the circuit functions unreliably due to leakage currents. In some prior transducer units, the prior flat spring is found to be corroded and loses elastic properties. The improved tocodynamometer transducer 100, in the present invention, overcome this moisture ingress shortcoming by way of setting process parameters for the injection molded parts so that the plastic top enclosure 106 and bottom enclosure 146 do not deform in manufacturing thus eliminating any gap that would allow moisture ingress. In addition, the bottom edge 148 is contoured to accept an o-ring 124 that further seals the seam between the top enclosure 106 and the bottom enclosure 146 when joined. This is extremely helpful in preventing moisture ingress proximate the cable hole 180 where cable 140 is installed and where a reduction in mechanical stress prevents cracks on the bottom enclosure near cable hole 180 which better prevents moisture intrusion resistance in the improved tocodynamometer transducer 100.

While prior transducers use ABS (Acrylonitrile butadiene styrene) resin for electrical connectors, such connector material can absorb moisture. In operation, such moisture in the connector material can lead to a leakage current between the electrical pins. This leakage current can vary depending on changes in humidity resulting in drift in the baseline of the waveform 324. In an exemplary embodiment, to further guard against moisture intrusion related drift and/or erratic operation, the electrical connectors in the improved tocodynamometer transducer 100 are fabricated from either PEEK (poly ether ether ketone) or PSU (Polysulfone) resin due to excellent electrical, physical properties, and resistance to moisture. These characteristics maintain high electrical impedance and electrical insulation between the contact pins in the electrical connectors.

In an exemplary embodiment, diaphragm 184 is circular in shape. Better illustrated in at least FIG. 10, the diaphragm 184 comprises a flexible relief channel 196 integrally formed in the diaphragm 184 proximate to the perimeter of the diaphragm 184 defining a diaphragm deflection area 139. The diaphragm 184 is secured within the diaphragm opening 141.

In an exemplary embodiment, diaphragm 184 can be an over-molded diaphragm with 60A shore hardness TPEE (Thermoplastic Polyester Elastomer) material to improve the overall performance—sensitivity, resilience, flexibility, abrasion, and solvent resistance (anti-bacterial/disinfectant), flex life for long durability and compliance to 3A sanitary standard. In other exemplary embodiment, the diaphragm 184 can be fabricated in other ways with other materials, as may be required and/or desired in a particular embodiment. The diaphragm 184 is secured within the diaphragm opening 141. More than one diaphragm anchor hole 194 aid in mechanically securing the diaphragm 184 to the bottom enclosure 146.

Figure 9:
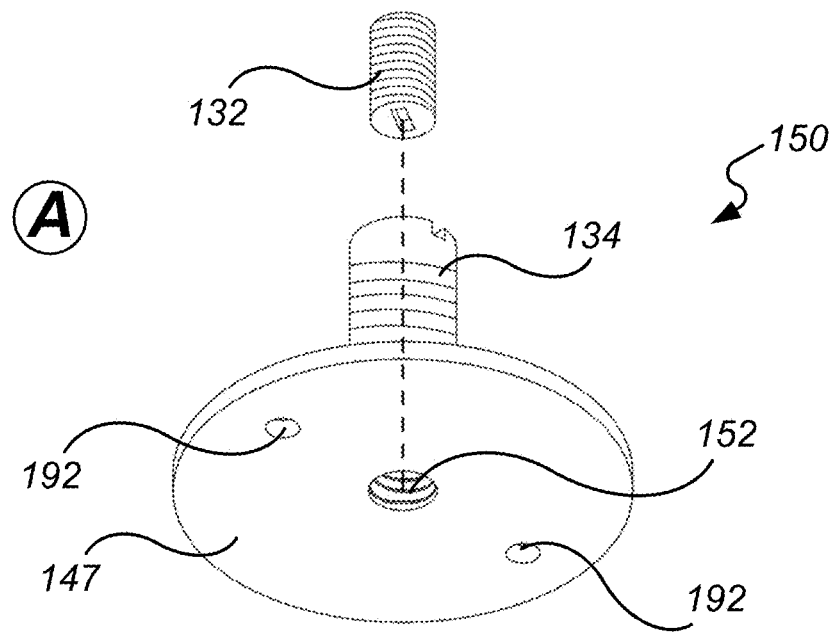
FIG. 9 illustrates one example of a plunger assembly.
Figure 9:
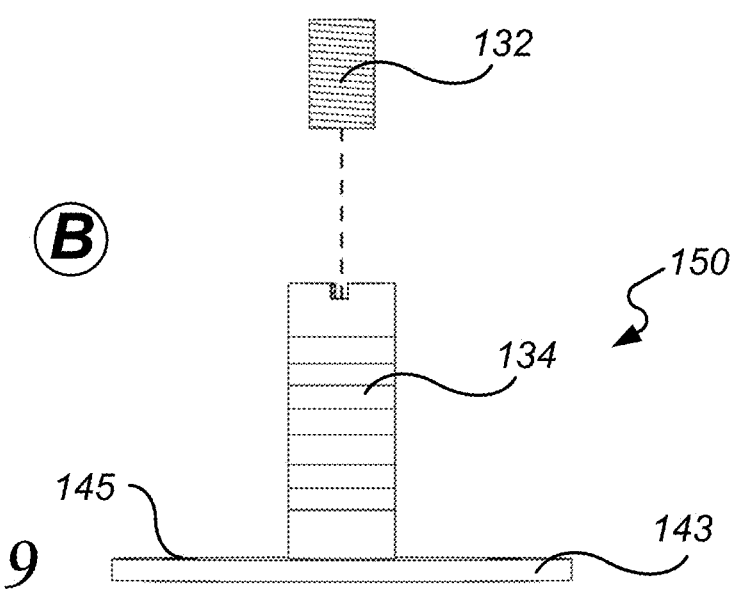

In an exemplary embodiment and as better illustrated in at least FIGS. 5 and 9, a plunger 150 comprises a shaft having a shaft hole 152 along the length of the shaft 134 that is threaded, and a deflection surface 143. The deflection surface 143 has a plunger top side 145 and a plunger bottom side 147. Manufacturing holes 192 are visible on the plunger bottom side 147. The plunger top side 145 and the plunger bottom side 147 are flat and absent raised embossed features. The deflection surface 143 is circular in shape and sized to substantially fit within the deflection area 139. Shaft 134 is circular in shape and uniform in diameter along the length of shaft 134. The shaft is integrally attached to the center of the plunger top side 145 forming a 90-degree angle between shaft 134 and deflection surface 143 around the circumference of shaft 134. The shaft 134 further comprises a thread pattern embossed around the outer circumference. In contrast shaft 150, in the present invention, is absent of any step ring 244 molding found in prior transducers. This is an advantage in the present invention as it increases the travel distance of the shaft 134 within the LVDT 120 which increases the dynamic range 504 of the improved tocodynamometer transducer 100.

In an exemplary embodiment and as better illustrated in at least FIGS. 5 and 9, a ferrite core 132 is threaded around the outer circumference and solid in composition. The ferrite core 132 is screwed into shaft hole 152. The length of the ferrite core 132, in the present invention, is on the order of 50% short in length than prior transducers 200. This shorter length of the ferrite core is essential to operate the LVDT in compliance with the fundamental measurement principle.

In an exemplary embodiment and as better illustrated in at least FIGS. 5 and 8, a transformer housing 130 is circular in shape. The transformer housing 130 comprises a housing bottom 11 having a housing hole 113 centrally located therethrough. An outer circumference surface 149, and a housing interior region 151. The housing bottom 11 has a diaphragm facing outer surface 163 that is flat and absent raised embossed features maximizing deflection distance between the plunger top side 145 and the diaphragm facing outer surface 163. More than one mounting tab 131 has a transformer housing mounting hole 129 therethrough. The mounting tabs 131 are integrally formed along the outer circumference surface 149. More than one magnetic shield standoff 127 is integrally formed in the housing interior region 151. More than one spring standoff 133 is integrally formed in the housing interior region 151. The threaded metal inserts 186 are fitted into each of the magnetic shield standoff 127 and the spring standoff 133.

Figure 12:
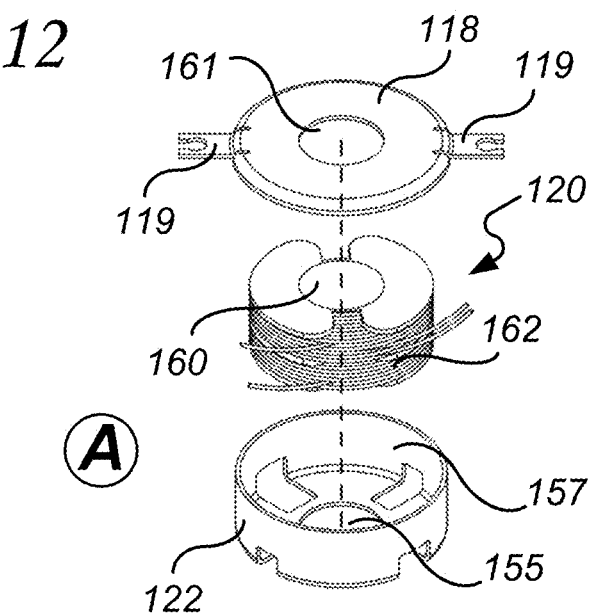
FIG. 12 illustrates one example of a magnetic shield enclosure assembly.
Figure 12:
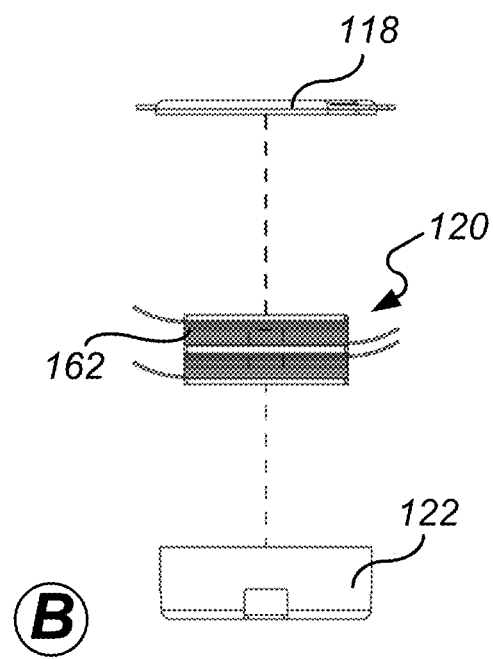

In an exemplary embodiment and better illustrated in at least FIGS. 2, 5, and 12, a linear variable differential transformer (LVDT) 120 has a circular air core 160, a top wire winding edge 156, and a bottom wire winding edge 158 that is defined by the location and length of a wire winding 162 around the circular air core 160. As better illustrated in at least FIG. 3, the plunger 150 transitions between a maximum deflection 312 (FIG. 3, reference 'C') and a minimum deflection 312 (FIG. 3, reference 'A'). During the maximum deflection, the ferrite core 132 is positioned below the top wire winding edge 156 and during a minimum deflection, the ferrite core 132 is positioned above the bottom wire winding edge 158. In this regard, the ferrite core 132 remains within the length of the wire winding 162 of the linear variable differential transformer 120 generating a linear voltage output 502 across the plunger 150 range of travel.

In an exemplary embodiment and with reference to at least FIGS. 5 and 12, a magnetic shield enclosure 118/122 comprises a top shield 118 having a top shield hole 161 that is centrally located and at least two shield mounting holes 119, and a bottom shield 122 having a shield interior region 157 and a bottom shield hole 155 that is centrally located. The bottom shield hole 155 is aligned with the top shield hole 161. The linear variable differential transformer 120 is fitted into the shield interior region 157 and the non-magnetic machine screw type of the metal fastener 116 passes through the shield mounting hole 119 and into the threaded metal inserts 125 that are fitted into the transformer mounting standoff 127 securing the magnetic shield enclosure 118/122 comprising the LVDT 120 to the transformer housing 130. The shaft 134 of the plunger 150 is placed through the housing hole 113, the bottom shield hole 155, the circular air core 160, and the top shield hole 161. The plunger bottom side 147 is placed in contact with the diaphragm deflection area 139 and the machine screw type of the metal fastener 126 is placed through the transformer housing mounting hole 129 and into the threaded metal insert 178 fitted into the transformer housing standoff 127 securing the transformer housing 130 and precisely aligning co-planar the deflection surface 143, the diaphragm facing outer surface 111, and the diaphragm deflection area 139.

Figure 7:
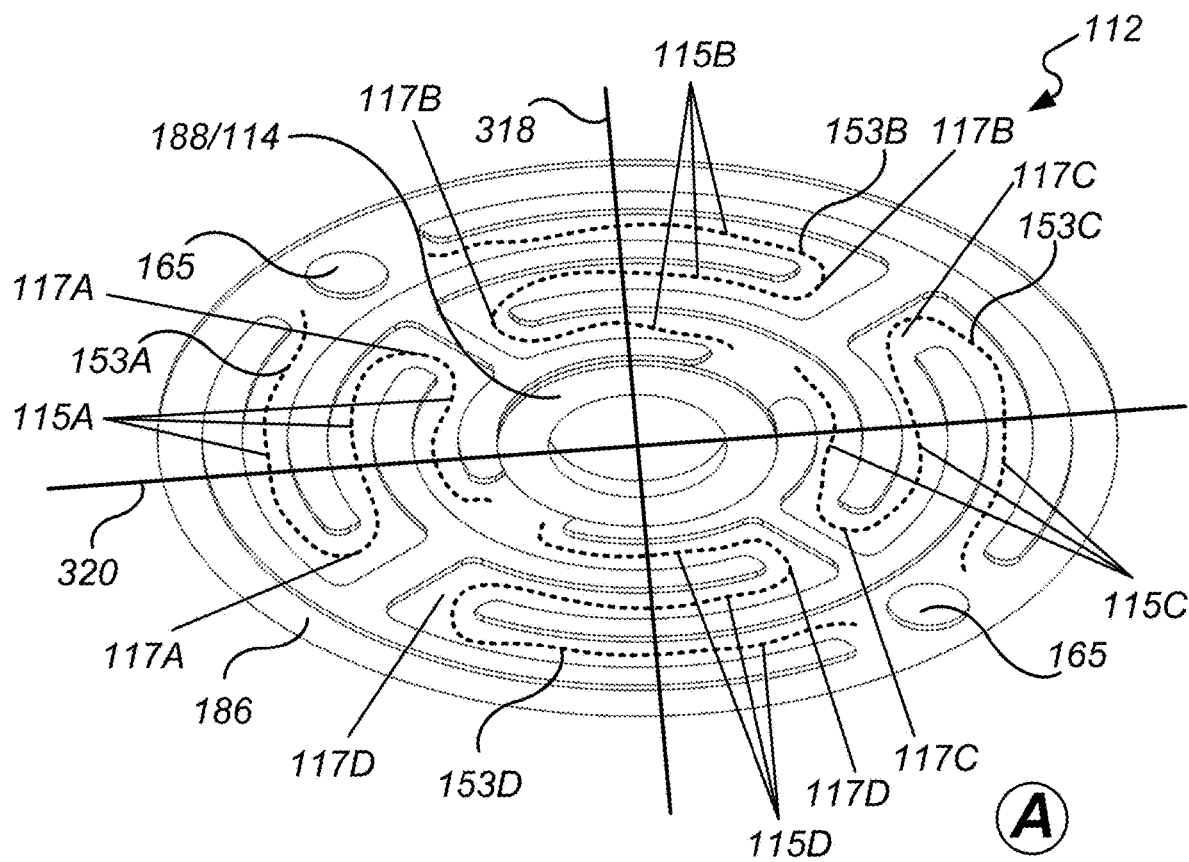
FIG. 7 illustrates one example of a flat spring.
Figure 7:
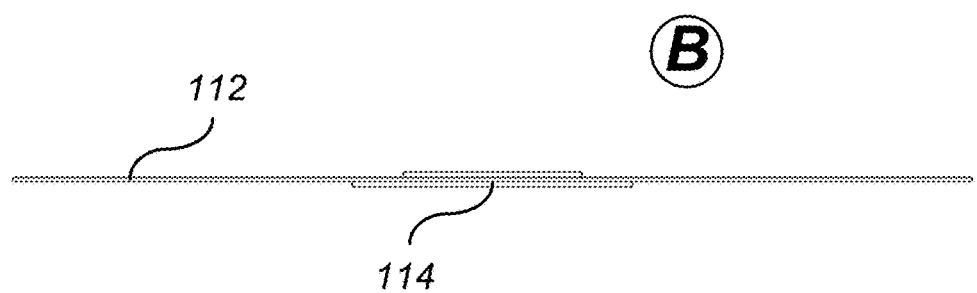

In an exemplary embodiment and with reference to at least FIG. 7, a flat spring 112 is formed from a single contiguous piece of metal. The flat spring 112 comprises an outer ring 190, an inner ring 188, and four spring ribs 153A-D. The outer ring 190 has more than one spring mount hole 165. Each of the spring ribs 153A-D (illustrated to easier see in FIG. 7 by dashed lines) is symmetrical, curvilinear in shape, identical in path length, separated by an air gap, and equally spaced between the outer ring 190, the inner ring 188, and the spring rib 153A-D that are adjacent. Each of the spring ribs 153A-D is connected, in an integrally formed manner, at a first end to the outer ring 190 and a second end to the inner ring 188. In this regard, the spring constant of the flat spring 112 is predetermined by the thickness of the flat spring 112 and identical along two or more axes 318 and 320 with respect to the inner ring 188.

In the present invention, the term "spring constant" is intended to mean a characteristic of a spring that measures the ratio of the force affecting the spring to the displacement caused by it. In other words, it describes how stiff a spring is and how much it will stretch or compress.

In prior transducers, the spring 210 is fastened to the plastic housing 226 using screws 208. The spring 112 contact area on the standoff is minimal on the edges with hollow space below due to deep molded-in metal inserts. The screws 208 put stress on the spring 210 and start loosening in a short span of time. This contributes to drift in the transducer output. The displacement of the flat spring 210 at the center due to stress after fastening with screws 208 also reduces the dynamic range and affects the linearity. In the present invention, in order to remove this stress, the threaded metal inserts are molded-in so that the top of the spring standoffs 133 and the threaded metal inserts 186 are flush providing maximum rigid surface contact in the horizontal plane for the flat spring 112.

In an exemplary embodiment and as better illustrated in at least FIGS. 5 and 7, a spring washer 114 comprises a threaded raised inner collar that is sized, fitted through the inner ring 188, and adhered to the flat spring 112 securing the spring washer 114. The surface of the spring washer 114 is flat and absent raised embossed features. The shaft 134 screws into and protrudes from the spring washer 114, machine screw type of the metal fasteners 110 are is placed through the spring mounting holes 110 and into the threaded metal inserts 186 that are in the spring standoff 133 securing the flat spring 112 and precisely aligning the spring washer co-planar with the deflection surface 143, the diaphragm facing outer surface 111, and the diaphragm deflection area 139. The top enclosure 106 and the bottom enclosure 146 are joined and secured together.

A method of precisely adjust the plunger 150 during calibration is by way of fine threads embossed on the plunger 150 shaft 134 threading into the threaded inner collar of the of the spring washer 114. In this regard, the plunger shaft 134 can be twisted, screwing into the spring washer 114 to adjust the gap 308/310 between the plunger top side 145 and the diaphragm facing outer surface 111 of the transformer housing 130. Such precise adjustments are on the order of micrometer steps that are made during calibration.

In addition, a cable o-ring 142 and a stainless-steel cable fastener 144 can be used to secure the wire cable 140 to the bottom enclosure 146. In this regard, the bottom enclosure 146 has a cable hole 180 through which the wire cable 140 is inserted. The wire cable 140 comprises a threaded end over which a cable o-ring 142 and a stainless-steel threaded fastener 144 secure the wire cable 140 to the bottom enclosure 146.

Referring to FIG. 6, there is illustrated a prior art tocodynamometer transducer. Two examples of a prior transducer 200 are the GE COROMETRICS NAUTILUS TOCO TRANSDUCER 2264LAX/HAX, and the Toco model Reference #2108347-001. Reference 'A' is a bottom perspective view of the LVDT housing 226.

These prior transducers 200 have several shortcomings including uterine contraction data being easily compromised by fluctuations in belt tension. If the labor is intense and the patient moves, belt tension changes continually. Hence for satisfactory operation, the patient must be kept relatively immobile. Once belt tension has been altered by patient movement, the belt tension must be readjusted otherwise no uterine activity data will be recovered. Additionally, when the patient is transferred from the labor ward to the delivery room the belt tension has to be readjusted.

Other common shortcomings of prior transducers are that most are strain gauge based. The thin film resistive strain gauges have disadvantages that include the inability to provide lower ranges, low-level outputs, high gain amplification needed, and hence lower stability, sensitivity to environmental vibration, long-term drift, creep due to adhesive agents, and other disadvantages.

Few of the prior transducers incorporate LVDT as the pressure sensor. LVDT advantages include LVDT-based transducers have low power consumption, higher sensitivity, fewer ruggedness/mechanical failures that are associated with strain gauges, a wider dynamic range of operation, low hysteresis, and other advantages.

There are some disadvantages of the LVDT-based transducers which include requiring a large primary voltage that can produce distortion in the output, temperature affecting the performance, and sensitivity to stray magnetic fields.

Shortcomings of prior transducers 200 include a wide variation in output (drift) and shorter dynamic range, with belt pressure almost the full dynamic range can be utilized, with some of the prior transducer units that have a plastic bottom case 238 with shorter internal height for the plunger 230 upward movement (stroke length for the plunger to move inside the LVDT bore) and hence sometimes uterine contractions are not sensed, and other shortcomings.

Additional shortcomings of prior transducers 200 include a wide variation in sensitivity and highly nonlinear output with drift over time, and the output offset voltage increases which after reaching a certain level the fetal monitor gives an error and stops sensing contraction waveform.

Additional shortcomings of prior transducers 200 include spurious or intermittent output even when there is no contraction taking place, and electromagnetic noise pick-up by the 9.5 mm in length ferrite core 228 which is longer than the 6 mm bore of the LVDT 222 causing large drifts in the output.

Additional shortcomings of prior transducers 200 include overall poor performance and intermittent non-operation causing discomfort to the pregnant patient as well as a hassle for the clinical staff as they need to perform frequent belt tension adjustment and repositioning.

Additional shortcomings of prior transducers 200 include in general self-tapping screws that loosen at PCB 216, LVDT housing 226, and flat spring 210 that impact plunger 230, and ferrite core 228 performance and accuracy making prior transducers 200 non-operable over time as the plunger loses coupling with the contraction sensing diaphragm.

Prior transducer 200 top 206 and bottom 238 are secured together with fasteners 204. In addition, the LVDT 222 is secured inside a metal enclosure 220/224. A cable 236 interconnects the prior transducer to external equipment.

Referring to FIG. 7, there is illustrated one example of a flat spring. Reference 'A' is a top perspective view and reference 'B' is a side view. In an exemplary embodiment, a flat spring 112 is formed from a single contiguous piece of metal. The flat spring 112 comprises an outer ring 190, an inner ring 188, and four spring ribs 153A-D. The outer ring 190 has more than one spring mount hole 165. Each of the spring rib 153A-D is symmetrical, curvilinear in shape, identical in path length, separated by an air gap, and equally spaced between the outer ring 190, the inner ring 188, and the spring rib 153A-D that are adjacent. Each of the spring ribs 153A-D (illustrated to easier see in FIG. 7 by dashed lines) is connected, in an integrally formed manner, at a first end to the outer ring 190 and a second end to the inner ring 188. In this regard, the spring constant of the flat spring 112 is predetermined by the thickness of the flat spring 112 and identical along two or more axes 318 and 320 with respect to the inner ring 188.

An advantage, in the present invention, of four equal spring ribs 153A-D, is that two equal and perpendicular axis 318/320 are formed. This keeps the flat spring 112 spring constant the same in the north, south, east, and west directions. The benefit is that forces applied on any perimeter of the diaphragm have the same spring constant of resistance and as such the improved tocodynamometer transducer 100 is equally accurate wherever the force of the contraction is applied on the diaphragm deflection area 139. In contrast and with reference to at least FIG. 6, prior transducers 200 have only one axis 306 of spring constant similarity. The prior flat spring 210 is connected in just two places between the inner and outer areas. Large air gaps 250 prevent symmetry in a two-axis direction. As a result, the same force in different locations on the prior diaphragm causes spring 210 to flex in different manners and with different spring constants. As such, the accuracy with regard to the application of the contraction force applied in different areas of the diaphragm produce different and inaccurate results.

In an exemplary embodiment, each of the spring ribs 153A-D can comprise two connecting segments 117A-D, and three curvilinear segments 115A-D, each of the curvilinear segments 115A-D match the curve of the outer ring 190 and inner ring 188 and are interconnected by at least one connecting segment 117A-D.

In prior transducers 200, the linearity suffers greatly from unit to unit as the prior flat spring 210 property (spring constant–displacement in micrometer/unit force) variation tolerance is more than 20% and it keeps deforming along the direction of applied force (axially upwards towards the plastic top case).

In the present invention, flat spring 112 overcomes the shortcomings of the prior flat spring 210 with tolerance less than 5% for the linear spring constant (displacement/applied force, 65 micrometer/100 gm) over a displacement length range of 800 micrometers. In operation, the maximum displacement of the flat spring 112 is in the range of 325 micrometers (which is less than 50% of full linear dynamic range capability) for an extended dynamic range of 500 gm force (approx. 160 gm/cm 2 pressure) on the plunger 150/diaphragm deflection area 139. This ensures that the 4.6 mm long ferrite core 134 installed at the center of the LVDT 120 transformer will remain between the top wire winding edge 156 and the bottom wire edge 158 while a full-scale dynamic range of 500 gm force is applied on the diaphragm deflection area 139 registering 200 Toco counts (Baseline default set to count 10+200) on calibrated fetal monitor display device 302. At this full-scale reading, the ferrite core will be 0.375 mm (375 micrometers) below the top wire winding edge 156 of the LVDT 120 air core 160 as well as 0.975 mm (975 micrometers) of its length will remain engaged with the lower secondary coil of LVDT (S1) linking more than 10% of the magnetic flux and hence the device will be fully operating in the linear range of the LVDT characteristic with high immunity to slow varying external magnetic field or electromagnetic interference (EMI) as the solid core will always remain inside the LVDT air core 160. Another advantage, is that the flat spring 120 will never deflect more than 50% of its extreme limit, so the spring constant and the flat spring elastic properties will not deteriorate over time and hence the overall performance of the improved tocodynamometer transducer 100 will be highly stable even after years of operation.

Another shortcoming of the prior flat spring 210 is that a prior plastic adapter 212 has prongs 242 that fit through holes in the prior spring 210. Once fitted, the prior plastic adapter 212 is affixed to the prior flat spring 210 by way of heat welding, melting the prongs 242, to prevent the removal of the adapter 212 from spring 210. Such heat welding introduces stresses in the prior flat spring 210 metal which reduces spring constant (which means a reduction in sensitivity) for the force measurement and reduces dynamic range. Reduced sensitivity also means missing weak to medium-strength contractions.

Referring to FIG. 8, there is illustrated one example of a transformer housing assembly. In an exemplary embodiment, a transformer housing 130 is circular in shape. The transformer housing 130 comprises a housing bottom 111 having a housing hole 113 centrally located therethrough. An outer circumference surface 149, and a housing interior region 151. The housing bottom 111 has a diaphragm facing outer surface 163 that is flat and absent raised embossed features maximizing deflection distance between the plunger top side 145 and the diaphragm facing outer surface 163. More than one mounting tab 131 has a transformer housing mounting hole 129 therethrough and are integrally formed along the outer circumference surface 149. More than one magnetic shield standoff 127 is integrally formed in the housing interior region 151. More than one spring standoff 133 is integrally formed in the housing interior region 151. The threaded metal inserts 186 are fitted into each of the magnetic shield standoffs 127 and the spring standoffs 133.

In an exemplary embodiment, the improved tocodynamometer transducer 100 incorporates two threaded metal threaded inserts 125 in the transformer housing 130 magnetic shield standoffs 127 that are stainless-steel machine threaded screws, 2-56×¼ inch. In contrast, prior transducers 200 use self-tapping aluminum screws 218 to fasten the LVDT assembly. The use of self-tapping screws 218 allows slow drift in the output and sporadic operation due to the loosening of the LVDT assembly 226 over time causing the relative position of the ferrite core 228 inside the plunger 230 to shift towards the lower LVDT coil/diaphragm (below null position) increasing the LVDT output voltage offset. The drift in LVDT output due to slowly increasing offset voltage proportional to LVDT assembly loosening in micrometers requires resetting the UA (uterine activity) reference/Toco baseline count on the fetal monitor and some of the fetal monitors, especially monitor models 170 series that do not sense the contractions at all as the offset voltage gets large enough to saturate the input stage of the fetal monitor when the LVDT loosens by just about 180 micrometers (0.18 mm) towards the plastic top case 206.

Prior transducers 200 use inserts to fasten the spring 210. These inserts are molded a little deeper leaving a hollow space between the top of the standoff and the top of the insert. When the spring 210 is fastened it only makes contact with the plastic rim not the top of the insert. Due to the hollow space, when the screws 208 are installed, it creates stress in the spring 210 and the screws 208 start loosening quickly causing drift in the output. The stress also results in the reduction of usable dynamic range in the linear region or useful stroke length of the spring 210. The present invention overcomes this shortcoming by using 4-40 threaded metal inserts 186 molded-in without a hollow space between the rim of the spring standoff 133 and the threaded insert 186. Absent the hollow space, the threaded metal inserts 186 are flushed with the spring standoff 133 top edge with more contact area with the flat spring 112 and hence eliminates the stress after screws 110 are installed.

Referring to FIG. 9, there is illustrated one example of a plunger 150 assembly. Prior transducers 200 use a ferrite core 228 length is 9.5 mm (9500 micrometers) whereas the LVDT bore length is 6 mm (6000 micrometers) hence the ferrite core 228 sticks out of the LVDT bore on both sides (top and bottom) when physically placed at the center (null position) corresponding to zero force on the diaphragm/plunger. This causes the LVDT to operate in the non-linear region of its characteristics. With force applied to the diaphragm/plunger, the magnetic core keeps on sticking out of the LVDT bore on the top side. This adds output drift due to EMI pick up by the ferrite core that sticks out of the LVDT bore resulting in spurious/intermittent behavior.

In contrast, an advantage, in the present invention, a solid ferrite core 132 is used with a length of 4 mm to 4.8 mm, 4.6 mm being optimal as it yields a stroke length of 0.7 mm (700 micrometers) when placed at the center of the LVDT 120 (null position as a home position) and when it is at the winding top edge 156 of the LVDT during operation, 0.6 mm length on the other side will remain engaged with the first secondary coil (S1) of the LVDT 120, coupling more than 10% of the magnetic flux which in turn means the operation will be on the linear portion of the LVDT characteristics. Ferrite core 132 being a solid core in place of the prior hollow core 228, also improves the LVDT 120 sensitivity on the order of millivolts (my) output produced in the secondary per volt excitation of primary per micrometer displacement of the magnetic core.

Figure 10:
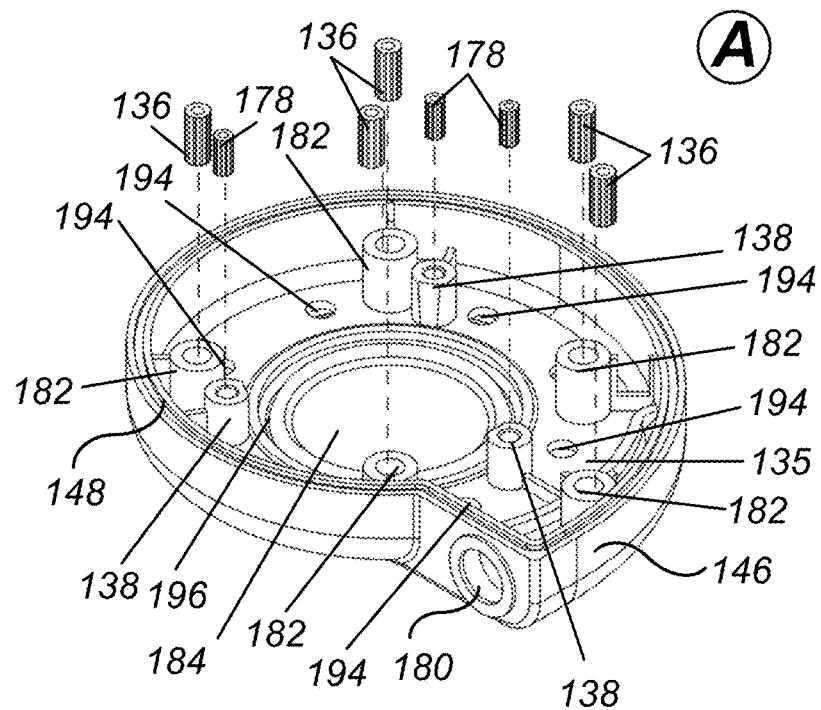
FIG. 10 illustrates one example of an enclosure bottom enclosure assembly.
Figure 10:
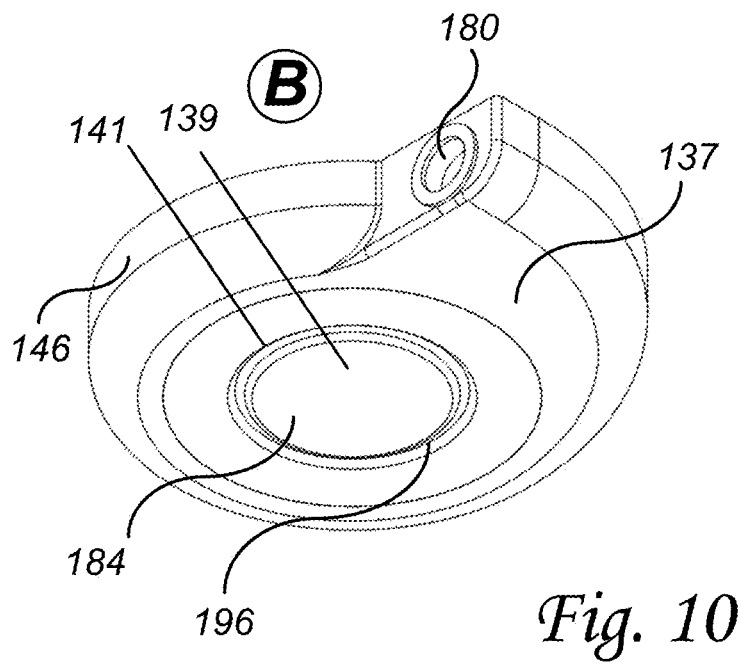

Referring to FIG. 10, there is illustrated one example of an enclosure bottom enclosure assembly. In an exemplary embodiment, diaphragm 184 is circular in shape. The diaphragm 184 comprises a flexible relief channel 196 integrally formed in the diaphragm 184 proximate to the perimeter of the diaphragm 184 defining a diaphragm deflection area 139. The diaphragm 184 is secured within the diaphragm opening 141. More than one diaphragm anchor hole 194 aid in mechanically securing the diaphragm 184 to the bottom enclosure 146.

Figure 11:
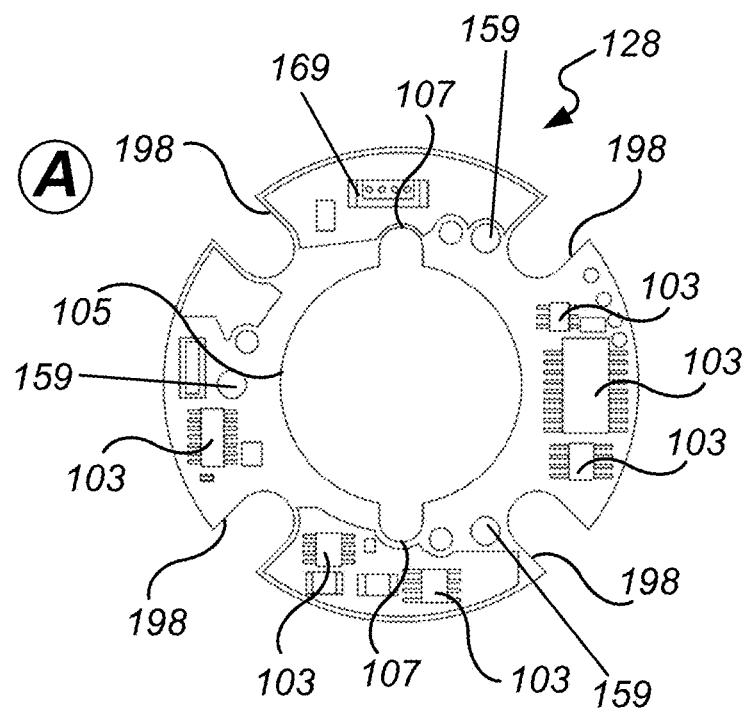
FIG. 11 illustrates one example of an electrical circuit on a printed circuit board.
Figure 11:
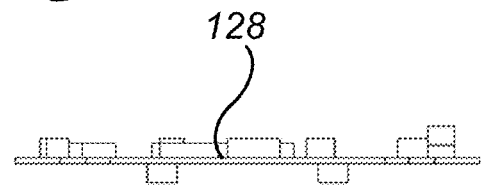

Referring to FIG. 11, there is illustrated one example of an electrical circuit 164 on a printed circuit board 128. In an exemplary embodiment, an electrical circuit 164 is configured on a printed circuit board 128. The printed circuit board 128 has a hollow center 105/107. The transformer housing 130 fits into the hollow center 105/107 and more than one printed circuit board mounting hole 159 aligns with the transformer housing mounting hole 129. More than one scalloped opening 198 along the perimeter of the printed circuit board 128 allows the standoff 166/182 to pass through without touching the printed circuit board 128. The printed circuit board 128 is secured with mounting tab 131 and printed circuit board standoffs 138. The electrical circuit 164 comprises more than one semiconductor 103. Each of the semiconductor 103 is rated for an operating voltage of +4.0 volts DC or less. The LVDT 120 is operationally related to the electrical circuit 164. The electrical circuit 164 receives the linear voltage output from the LVDT, generates a conditioned Vout linear voltage output signal 502, and communicates the Vout linear voltage output signal 502 by way of a wire cable 140 to a display device 302.

Referring to FIG. 12, there is illustrated one example of a magnetic shield enclosure 118/122 assembly. In an exemplary embodiment, the LVDT 120 is encased in a mu-metal magnetic shield 118/122 and fastened into the transformer housing 130.

Figure 13:
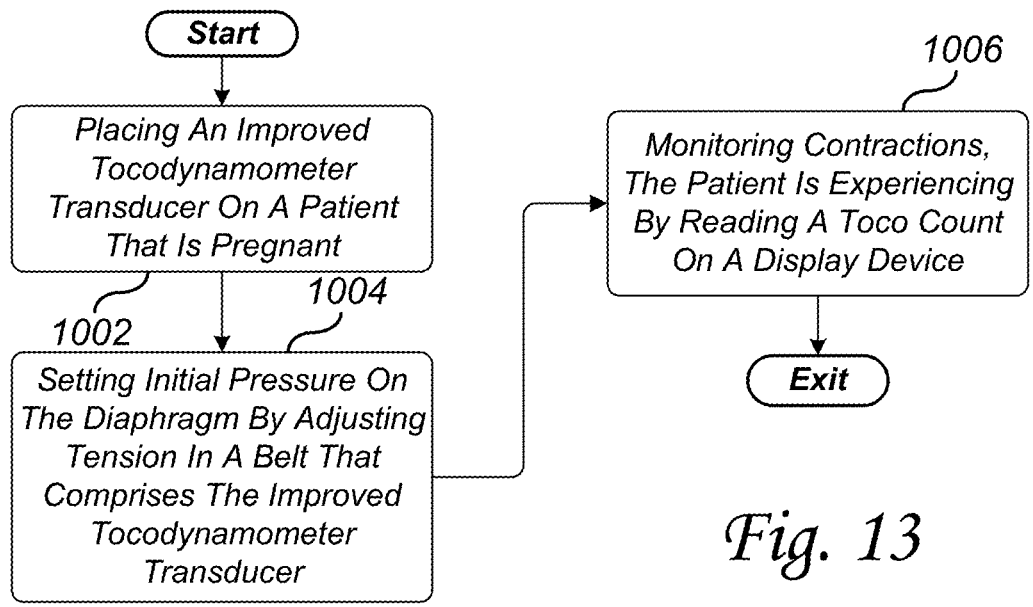
FIGS. 13-15 illustrates examples of a method of using an improved tocodynamometer transducer.

Referring to FIG. 13, there is illustrated one example of a method of using an improved tocodynamometer transducer 100. In an exemplary embodiment, the improved tocodynamometer transducer 100 can be used with patient 402 to monitor contractions 316. The method begins in step 1002 by placing the improved tocodynamometer transducer 100 on a pregnant patient 402 with diaphragm 184 in contact with the skin of patient 402 proximate to baby 404. The method then moves to step 1004.

In step 1004, the initial pressure on the diaphragm 184 is set by adjusting the tension in belt 314. The belt 314 comprises the improved tocodynamometer transducer 100 that is fastened around patient 402 so that absent contractions the Toco reading is set to either 10 or 20 Toco count as a base line reference. The method then moves to step 1006.

In step 1006, contractions that patient 402 is experiencing are monitored by recording a Toco count on a display device 302. The method is then exited.

Figure 14:
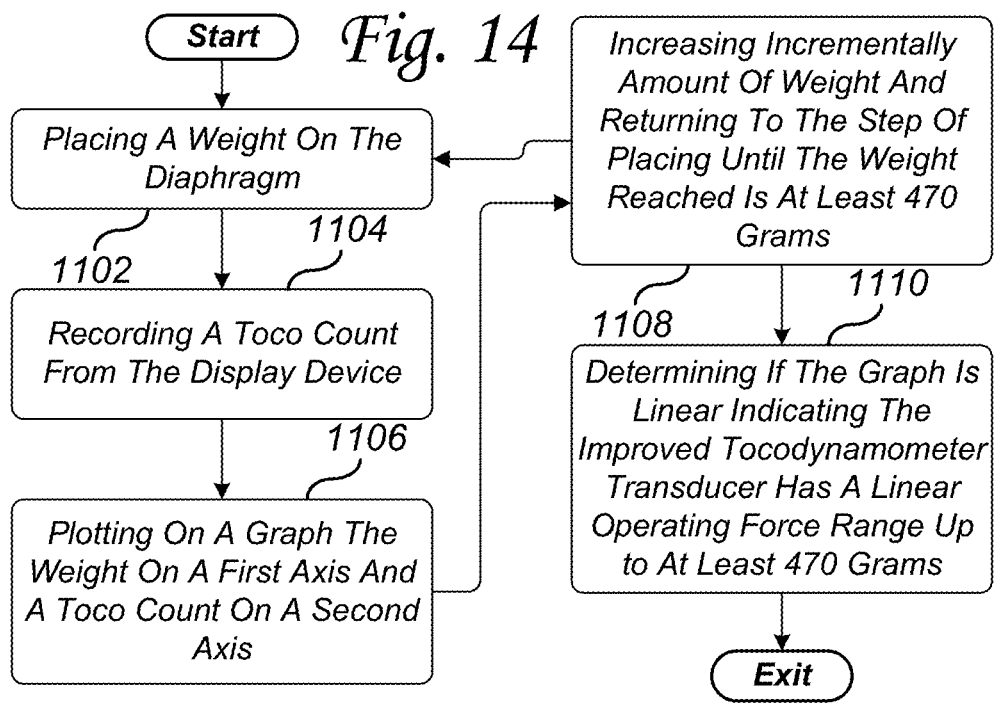

Referring to FIG. 14, there is illustrated one example of a method of using an improved tocodynamometer transducer 100. The calibration procedure given in the GE document (2003704-001) using a single metallic 52.5 gm weight, is not adequate to ensure a fully functional dynamic range of contraction measurement and reliability as it does single measurement reading using this standard weight supplied/recommended by GE. The calibration by using this metallic weight is not at all accurate as the metal disturbs the magnetic field of LVDT causing a large error in Toco count reading (more than 80%) and common mode rejection (CMR) voltage adjustment is always 'off' from the actual value required. There is no test specified in any of the GE calibration check procedures for the output drift or stability assessment. At some stage, GE revised the calibration test procedure in service manuals of the latest fetal monitors (model 170 series, service manual P/N 2000947-00, Revision C, page 152, Section 7-20) to use 52.5 gm, 100 gm, and 150 gm Teflon weight to check dynamic range of 63 Toco counts. This too is not adequate to ensure full dynamic range but it improves accuracy for CMR voltage adjustment as Teflon does not disturb the magnetic field.

Strong uterine contraction results in pressure in the range of 100 gm/cm$^2$ on the abdomen. The dynamic full-range sensing capability of the prior transducer should be at least 100 gm/cm$^2$. The pressure-sensing plunger (coupled with a rubber diaphragm) has an effective radius of approximately 1 cm. That means the pressure sensing area is about 3.14 cm 2 and hence 314 gm of weight placed on the diaphragm would produce a pressure of about 100 gm/cm$^2$. Adjust the gain on the PCB so that calibrated fetal monitor displays Toco count 126 (Baseline count 10+126=136)+/−2 when 315 gm weight is placed on the diaphragm. This is a full-scale or Single Dynamic Range reading. Take the Toco count reading for various weight values 10, 20, 40, 50, 100, 200, 300, 400, and 500 gm to make sure it is linear. The sample testing data in FIG. 16 illustrates that the improved tocodynamometer transducer 100 is linear with sensitivity to 12.5 gm force (approximate pressure of 4 gm/cm$^2$). Toco count linearity with pressure increase and a higher dynamic range than 100 gm/cm$^2$ is important as there will be initial pressure on the diaphragm due to the belt tension while in actual usage (monitoring expectant mom). The 500 gm weight will produce a pressure of approximately 160 gm/sq. cm. and Toco count should be in the range of 200. Old fetal monitor models such as 115, 116, and 118 have 199 Toco counts (baseline default count 10+189) and hence full-scale measurement should be taken by placing 470 gm standard weight that should give 188 Toco counts (base count 10+188=198). If this calibration and testing process is not followed or sticking to just one reading of 52.5 gm weight as per GE document (2003704-001) as well as the latest procedure of using 3 Teflon weights (52.5 gm, 100 gm, 150 gm), we would never know whether the transducer has enough dynamic range to sense the pressure or not. It may get used up completely due to belt pressure resulting in no record of contractions.

In an exemplary embodiment, two sets of linearity test results 322/324 as an example of the present method are illustrated in FIG. 16. The method begins in step 1102 by placing a weight on the diaphragm. The method then moves to step 1104.

In step 1104 a Toco count is recorded from the display device. The method then moves to step 1106.

In step 1106, the weight on the first axis and the Toco count on the second axis is plotted on a graph. The method then moves to step 1108.

In step 1108, the amount of the weight is increased incrementally. The method then returns to step 1102 of placing, until the amount of the weight reached is at least 470 grams. The method then moves to step 1110.

In step 1110, a determination is made if the graph is linear indicating the improved tocodynamometer transducer 100 has a linear operating diaphragm force range up to at least 470 grams. The method is then exited.

Figure 15:
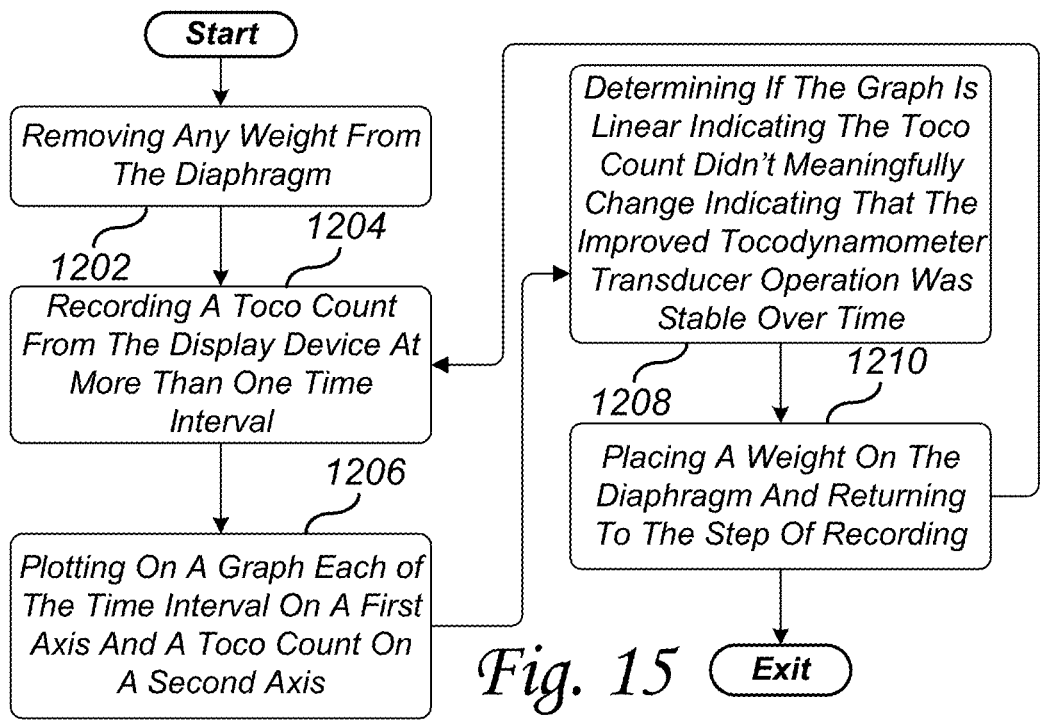

Referring to FIG. 15, there is illustrated one example of a method of using an improved tocodynamometer transducer. In an exemplary embodiment, two sets of stability test results 326/328 as an example of the present method are illustrated in FIG. 16. The stability test measures changes in output over time. The method begins in step 1202 by removing any weight from the diaphragm at a start time. The method then moves to step 1204.

In step 1204, a Toco count is recorded from the display device at more than one time interval between a start time and a finish time. The method then moves to step 1206.

In step 1206, each of the time intervals on the first axis and the Toco count on the second axis is plotted on a graph. The method then moves to step 1208.

In step 1208, a determination is made if the graph is linear indicating the Toco count did not meaningfully change between the start time and the finish time indicating that the improved tocodynamometer transducer 100 operation was stable over time. The method then moves to step 1210.

In step 1210, a weight is placed on the diaphragm and the method returns to step 1204 of recording.

The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered a part of the claimed invention.

While the preferred embodiment of the invention has been described, it will be understood that those skilled in the art, both now and in the future, may make various improvements and enhancements which fall within the scope of the claims which follow. These claims should be construed to maintain the proper protection for the invention first described.

What is claimed is:

1. An improved tocodynamometer transducer comprising:
 a bottom enclosure having a bottom internal side, a skin-contacting side, and a diaphragm opening therethrough;
 a top enclosure having a top exterior surface and a top internal surface;
 a diaphragm is circular in shape, the diaphragm comprises a flexible relief channel integrally formed in the diaphragm proximate to perimeter of the diaphragm defining a diaphragm deflection area, the diaphragm is secured within the diaphragm opening;
 a plunger comprises a shaft having a shaft hole along length of the shaft that is threaded, and a deflection surface having a plunger top side and a plunger bottom side;
 a ferrite core is threaded around outer circumference and solid in composition, the ferrite core is screwed into the shaft hole;
 a transformer housing comprises a housing bottom having a housing hole centrally located therethrough, an outer circumference surface, and a housing interior region;
 a linear variable differential transformer having a circular air core;
 a magnetic shield enclosure comprises a top shield having a top shield hole, and a bottom shield having a shield interior region, the linear variable differential transformer is fitted into the shield interior region, the shaft of the plunger is placed through the housing hole, the bottom shield hole, the circular air core, and the top shield hole, the magnetic shield enclosure is fastened in the housing interior region, the plunger bottom side is placed in contact with the diaphragm deflection area;

a flat spring is formed from single contiguous piece of metal, the flat spring comprises an outer ring, an inner ring, and four of a spring rib, the outer ring having more than one of a spring mounting hole, each of the spring rib is symmetrical, curvilinear in shape, identical in path length, separated by an air gap, and equally spaced between the outer ring, the inner ring, and the spring rib that are adjacent, each of the spring rib is connected, in integrally formed manner, at a first end to the outer ring and a second end to the inner ring, wherein spring constant of the flat spring is predetermined by thickness of the flat spring and identical along two or more axes with respect to the inner ring; and a spring washer comprises a threaded raised inner collar that is sized, fitted through the inner ring, and adhered to the flat spring, the shaft screws into and protrudes from the spring washer, the flat spring is fastened to the transformer housing, the top enclosure and the bottom enclosure are joined and secured together.

2. The improved tocodynamometer transducer in accordance with claim 1, the spring rib further comprises two of a connecting segment, and three of a curvilinear segment, each of the curvilinear segment match curve of the outer ring and inner ring and are interconnected by at least one of the connecting segment.

3. The improved tocodynamometer transducer in accordance with claim 1, further comprises one of the following:
the top enclosure further comprises more than one of a metal fastener; and
the top enclosure further comprises more than one of a threaded metal insert, the bottom enclosure further comprises more than one of a printed circuit board standoff that is integrally formed on the bottom internal surface, the top enclosure further comprises the threaded metal insert, the threaded metal insert is fitted into each of the printed circuit board standoff, more than one of a standoff is integrally formed on the top internal surface and the bottom internal surface, each of the standoff on the top internal surface is conical in shape and wider at the attachment point on the top internal surface, the top side comprises more than one fastener hole integrally formed, tapered, and countersunk, the threaded metal insert is fitted into each of the standoff on the bottom internal surface, each of the fastener hole is aligned with each of the standoff when the top enclosure and the bottom enclosure are joined, each machine screw type of the metal fastener passes through the fastener hole and into the threaded metal insert securing the top enclosure and bottom enclosure together.

4. The improved tocodynamometer transducer in accordance with claim 3, the plunger top side and the plunger bottom side are flat and absent raised embossed features, the deflection surface is circular in shape and sized to substantially fit within the deflection area, the shaft is circular in shape and uniform in diameter along length of the shaft, the shaft is integrally attached to center of the plunger top side forming a 90-degree angle between the shaft and the deflection surface around circumference of the shaft, the shaft further comprises a thread pattern embossed around outer circumference, the shaft having a shaft hole along length of the shaft, the shaft hole is threaded.

5. The improved tocodynamometer transducer in accordance with claim 4, the transformer housing is circular in shape, the housing bottom having a diaphragm facing outer surface that is flat and absent raised embossed features maximizing deflection distance between the plunger top side and the diaphragm facing outer surface, more than one of a mounting tab having a transformer housing mounting hole therethrough, the mounting tab is integrally formed along the outer circumference surface, more than one magnetic shield standoff and more than one of a spring standoff is integrally formed in the housing interior region, the threaded metal insert is fitted into each of the magnetic shield standoff and the spring standoff.

6. The improved tocodynamometer transducer in accordance with claim 5, the linear variable differential transformer having a top wire winding edge and a bottom wire winding edge that is defined by location and length of a wire winding around the circular air core, the plunger transitions between a maximum deflection and a minimum deflection, during the maximum deflection the ferrite core is positioned below the top wire winding edge and during a minimum deflection the ferrite core is positioned above the bottom wire winding edge, wherein the ferrite core remains within length of the wire winding of the linear variable differential transformer generating a linear voltage output across the plunger range of travel.

7. The improved tocodynamometer transducer in accordance with claim 6, the top shield having a top shield hole that is centrally located and at least one of a shield mounting hole, and the bottom shield having a bottom shield hole that is centrally located, the bottom shield hole is aligned with the top shield hole, non-magnetic machine screw type of the metal fastener passes through the shield mounting hole and into the threaded metal insert that is fitted into the transformer mounting standoff securing the linear variable differential transformer to the transformer housing, machine screw type of the metal fastener is placed through the transformer housing mounting hole and into the threaded metal insert fitted into the transformer housing standoff securing the transformer housing and precisely aligning co-planar the deflection surface, the diaphragm facing outer surface, and the diaphragm deflection area.

8. The improved tocodynamometer transducer in accordance with claim 7, surface of the spring washer is flat and absent raised embossed features, machine screw type of the metal fastener is placed through the spring mounting hole and into the threaded metal insert that is in the spring standoff securing the flat spring, and precisely aligning the flat spring co-planar with the deflection surface, the diaphragm facing outer surface, and the diaphragm deflection area.

9. The improved tocodynamometer transducer in accordance with claim 8, further comprising:
an electrical circuit is configured on a printed circuit board, the printed circuit board having a hollow center, the transformer housing fits into the hollow center and more than one of a printed circuit board mounting hole aligns with the transformer housing mounting hole, and more than one of a scalloped opening along perimeter of the printed circuit board allowing the standoff to pass through without touching the printed circuit board, the printed circuit board is secured on top of the mounting tab and the standoff, the electrical circuit comprises more than one of a semiconductor, each of the semiconductor is rated for operating voltage of +4.0 volts DC or less, the linear variable differential transformer is operationally related to the electrical circuit, the electrical circuit receives the linear voltage output, generates a conditioned linear voltage output signal, and communicates the conditioned linear voltage output signal by way of a wire cable to a display device.

10. The improved tocodynamometer transducer in accordance with claim 9, the bottom enclosure having a cable hole through which the wire cable is inserted, the wire cable comprising a threaded end over which a cable o-ring and a stainless-steel threaded fastener secure the wire cable to the bottom enclosure.

11. The improved tocodynamometer transducer in accordance with claim 1, the bottom enclosure having a recessed groove along the perimeter, an o-ring is fitted into the recessed groove, wherein when the top enclosure and the bottom enclosure are joined a water-tight seal is formed therebetween.

12. The improved tocodynamometer transducer in accordance with claim 1, the top enclosure further comprises one of the following:
   integrally formed one or more of a belt loop; or
   a top exterior surface and a top interior surface, a button standoff is integrally formed on the top exterior surface, the threaded metal insert is fitted into the button standoff from the top interior surface, and a threaded button is inserted through the top exterior surface into the threaded metal insert that is fitted inside the button standoff; or
   a top exterior surface, a top interior surface, and integrally formed one or more of the belt loop, a button standoff is integrally formed on the top interior surface, the threaded metal insert is fitted into the button standoff from the top interior surface, a threaded button is inserted through the top exterior surface into the threaded metal insert that is fitted inside the button standoff.

13. An improved tocodynamometer transducer comprising:
   more than one of a metal fastener;
   more than one of a threaded metal insert;
   a bottom enclosure having a bottom internal side, a skin-contacting side, and a diaphragm opening therethrough;
   a top enclosure having a top exterior side and a top internal side, more than one of a standoff is integrally formed on the top internal surface and the bottom internal surface, each of the standoff on the top internal surface is conical in shape and wider at the attachment point on the top internal surface, the threaded metal insert is fitted into each of the standoff on the bottom internal surface;
   a diaphragm is circular in shape, the diaphragm comprises a flexible relief channel integrally formed in the diaphragm proximate to perimeter of the diaphragm defining a diaphragm deflection area, the diaphragm is secured within the diaphragm opening;
   a plunger comprises a shaft having a shaft hole along length of the shaft that is threaded, and a deflection surface having a plunger top side and a plunger bottom side, the plunger top side and the plunger bottom side are flat and absent raised embossed features, the deflection surface is circular in shape and sized to substantially fit within the deflection area, the shaft is circular in shape and uniform in diameter along length of the shaft, the shaft is integrally attached to center of the plunger top side forming a 90-degree angle between the shaft and the deflection surface around circumference of the shaft, the shaft further comprises a thread pattern embossed around outer circumference;
   a ferrite core is threaded around outer circumference and solid in composition, the ferrite core is screwed into the shaft hole;
   a transformer housing is circular in shape, the transformer housing comprises a housing bottom having a housing hole centrally located therethrough, an outer circumference surface, and a housing interior region, the housing bottom having a diaphragm facing outer surface that is flat and absent raised embossed features maximizing deflection distance between the plunger top side and the diaphragm facing outer surface, more than one mounting tab having a transformer housing mounting hole therethrough, the mounting tab is integrally formed along the outer circumference surface, more than one of a magnetic shield standoff and more than one of a spring standoff are integrally formed in the housing interior region, the threaded metal insert is fitted into each of the magnetic shield standoff and the spring standoff;
   a linear variable differential transformer having a circular air core, a top wire winding edge and a bottom wire winding edge that is defined by location and length of a wire winding around the circular air core, the plunger transitions between a maximum deflection and a minimum deflection, during the maximum deflection the ferrite core is positioned below the top wire winding edge and during a minimum deflection the ferrite core is positioned above the bottom wire winding edge, wherein the ferrite core remains within length of the wire winding of the linear variable differential transformer generating a linear voltage output across the plunger range of travel;
   a magnetic shield enclosure comprises a top shield having a top shield hole that is centrally located and at least one shield mounting hole, and a bottom shield having a shield interior region and a bottom shield hole that is centrally located, the bottom shield hole is aligned with the top shield hole, the linear variable differential transformer is fitted into the shield interior region and non-magnetic machine screw type of the metal fastener passes through the shield mounting hole and into the threaded metal insert that are fitted into the transformer mounting standoff securing the linear variable differential transformer to the transformer housing, the shaft of the plunger is placed through the housing hole, the bottom shield hole, the circular air core, and the top shield hole, the plunger bottom side is placed in contact with the diaphragm deflection area and machine screw type of the metal fastener is placed through the transformer housing mounting hole and into the threaded metal insert fitted into the transformer housing standoff securing the transformer housing and precisely aligning co-planar the deflection surface, the diaphragm facing outer surface, and the diaphragm deflection area;
   a flat spring is formed from single contiguous piece of metal, the flat spring comprises an outer ring, an inner ring, and four of a spring rib, the outer ring having more than one of a spring mounting hole, each of the spring rib is symmetrical, curvilinear in shape, identical in path length, separated by an air gap, and equally spaced between the outer ring, the inner ring, and the spring rib that are adjacent, each of the spring rib is connected, in integrally formed manner, at a first end to the outer ring and a second end to the inner ring, wherein spring constant of the flat spring is predetermined by thickness of the flat spring and identical along two or more axes with respect to the inner ring;

a spring washer comprises a threaded raised inner collar that is sized, fitted through the inner ring, and adhered to the flat spring, surface of the spring washer is flat and absent raised embossed features, the shaft screws into and protrudes from the spring washer, machine screw type of the metal fastener is placed through the spring mounting hole and into the threaded metal insert that is in the spring standoff securing the flat spring and precisely aligning the spring washer co-planar with the deflection surface, the diaphragm facing outer surface, and the diaphragm deflection area, the top enclosure and the bottom enclosure are joined and secured together.

14. The improved tocodynamometer transducer in accordance with claim 13, the spring rib further comprises two of a connecting segment, and three of a curvilinear segment, each of the curvilinear segment match curve of the outer ring and inner ring and are interconnected by at least one of the connecting segment.

15. The improved tocodynamometer transducer in accordance with claim 13, the top exterior surface comprises more than one fastener hole aligned with the standoff on the top internal surface, the fastener hole is tapered and countersunk, the threaded metal insert is fitted into each of the standoff on the bottom internal surface, each of the standoff on the top interior surface and the bottom interior surface is aligned such that when the top enclosure and the bottom enclosure are joined, each machine screw type of the metal fastener passes through the fastener hole and into the threaded metal insert securing the top enclosure and bottom enclosure together.

16. The improved tocodynamometer transducer in accordance with claim 15, further comprising:

an electrical circuit is configured on a printed circuit board, the printed circuit board having a hollow center, the transformer housing fits into the hollow center and more than one of a printed circuit board mounting hole aligns with the transformer housing mounting hole, and more than one of a scalloped opening along perimeter of the printed circuit board allowing the standoff to pass through without touching the printed circuit board, the printed circuit board is secured on top of the mounting tab and the standoff, the electrical circuit comprises more than one of a semiconductor, each of the semiconductor is rated for operating voltage of +4.0 volts DC or less, the linear variable differential transformer is operationally related to the electrical circuit, the electrical circuit receives the linear voltage output, generates a conditioned linear voltage output signal, and communicates the conditioned linear voltage output signal by way of a wire cable to a display device.

17. The improved tocodynamometer transducer in accordance with claim 16, the bottom enclosure having a cable hole through which the wire cable is inserted, the wire cable comprising a threaded end over which a cable o-ring and a stainless-steel threaded fastener secure the wire cable to the bottom enclosure.

18. The improved tocodynamometer transducer in accordance with claim 13, further comprises one of the following:

the top enclosure further comprises integrally formed one or more of a belt loop; or the top enclosure further comprises a top exterior surface and a top interior surface, a button standoff is integrally formed on the top exterior surface, the threaded metal insert is fitted into the button standoff from the top interior surface, and a threaded button is inserted through the top exterior surface into the threaded metal insert that is fitted inside the button standoff; or the top enclosure further comprises a top exterior surface, a top interior surface, and integrally formed one or more of the belt loop, a button standoff is integrally formed on the top interior surface, the threaded metal insert is fitted into the button standoff from the top interior surface, a threaded button is inserted through the top exterior surface into the threaded metal insert fitted that is inside the button standoff.

19. The improved tocodynamometer transducer in accordance with claim 13, the bottom enclosure having a recessed groove along the perimeter, an o-ring is fitted into the recessed groove, wherein when the top enclosure and the bottom enclosure are joined a water-tight seal is formed therebetween.

20. A method of using an improved tocodynamometer transducer comprising the steps of:

providing an improved tocodynamometer transducer, the improved tocodynamometer transducer comprising an electric circuit, a bottom enclosure having a bottom internal side, a skin-contacting side, and a diaphragm opening therethrough, a top enclosure having a top exterior surface and a top internal surface, a diaphragm is circular in shape, the diaphragm comprises a flexible relief channel integrally formed in the diaphragm proximate to perimeter of the diaphragm defining a diaphragm deflection area, the diaphragm is secured within the diaphragm opening, a plunger comprises a shaft having a shaft hole along length of the shaft that is threaded, and a deflection surface having a plunger top side and a plunger bottom side, a ferrite core is threaded around outer circumference and solid in composition, the ferrite core is screwed into the shaft hole, a transformer housing comprises a housing bottom having a housing hole centrally located therethrough, an outer circumference surface, and a housing interior region, a linear variable differential transformer having a circular air core, a magnetic shield enclosure comprises a top shield having a top shield hole, and a bottom shield having a shield interior region, the linear variable differential transformer is fitted into the shield interior region, the shaft of the plunger is placed through the housing hole, the bottom shield hole, the circular air core, and the top shield hole, the magnetic shield enclosure is fastened in the housing interior region, the plunger bottom side is placed in contact with the diaphragm deflection area, a flat spring is formed from single contiguous piece of metal, the flat spring comprises an outer ring, an inner ring, and four of a spring rib, the outer ring having more than one of a spring mounting hole, each of the spring rib is symmetrical, curvilinear in shape, identical in path length, separated by an air gap, and equally spaced between the outer ring, the inner ring, and the spring rib that are adjacent, each of the spring rib is connected, in integrally formed manner, at a first end to the outer ring and a second end to the inner ring, wherein spring constant of the flat spring is predetermined by thickness of the flat spring and identical along two or more axis with respect to the inner ring, and a spring washer comprises a threaded raised inner collar that is sized, fitted through the inner ring, and adhered to the flat spring, the shaft screws into and protrudes from the spring washer, the flat spring is fastened to the transformer housing, the top enclosure and the bottom enclosure are joined and secured together;

placing a weight on the diaphragm;

recording a toco count from a display device, the linear variable differential transformer generates a linear voltage output that is proportional to the weight on the diaphragm, the linear voltage output is converted to a conditioned linear voltage output signal by the electric circuit, and the conditioned linear voltage output signal is communicated by way of a wire cable to the display device, the display device converts the conditioned linear voltage output signal to the toco count;

plotting on a graph the weight on a first axis and the toco count or selectively the conditioned linear voltage output signal on a second axis;

increasing incrementally amount of the weight and returning to the step of placing until amount of the weight reached is at least 470 grams; and determining if the graph is linear indicating the improved tocodynamometer transducer has a linear operating diaphragm force range of up to at least 470 grams.

* * * * *